(12) United States Patent
Hentrich et al.

(10) Patent No.: US 11,674,164 B2
(45) Date of Patent: Jun. 13, 2023

(54) PERIPLASMIC FUSION PROTEINS

(71) Applicant: BIO-RAD ABD SEROTEC GMBH, Puchheim (DE)

(72) Inventors: Christian-Michael Aloisius Heinz Hentrich, Munich (DE); Francisco Ylera, Munich (DE); Hans Joachim Knappik, Moorenweis (DE)

(73) Assignee: BIO-RAD ABD SEROTEC GMBH, Puchheim (DE)

( * ) Notice: Subject to any disclaimer, the term of this patent is extended or adjusted under 35 U.S.C. 154(b) by 431 days.

(21) Appl. No.: 16/822,102

(22) Filed: Mar. 18, 2020

(65) Prior Publication Data
US 2020/0299746 A1   Sep. 24, 2020

Related U.S. Application Data

(60) Provisional application No. 62/819,758, filed on Mar. 18, 2019.

(51) Int. Cl.
| | | |
|---|---|---|
| *C12P 21/02* | (2006.01) | |
| *C07K 16/00* | (2006.01) | |
| *C12N 1/20* | (2006.01) | |
| *C12R 1/19* | (2006.01) | |

(52) U.S. Cl.
CPC ............ *C12P 21/02* (2013.01); *C07K 16/00* (2013.01); *C12N 1/20* (2013.01); *C12N 1/205* (2021.05); *C07K 2317/522* (2013.01); *C07K 2317/55* (2013.01); *C07K 2317/622* (2013.01); *C07K 2319/00* (2013.01); *C12R 2001/19* (2021.05)

(58) Field of Classification Search
None
See application file for complete search history.

(56) References Cited

U.S. PATENT DOCUMENTS

| | | | |
|---|---|---|---|
| 5,264,365 | A | 11/1993 | Georgiou et al. |
| 6,828,121 | B2 | 12/2004 | Chen |
| 8,216,822 | B2 | 7/2012 | Mehta et al. |
| 8,969,038 | B2 | 3/2015 | Ellis et al. |
| 8,969,039 | B2 | 3/2015 | Ellis et al. |
| 9,109,216 | B2 | 8/2015 | Ellis et al. |
| 9,481,715 | B2 | 11/2016 | Vernet et al. |
| 9,547,003 | B2 | 1/2017 | Howarth |
| 9,688,775 | B2 | 6/2017 | Simmons et al. |
| 9,725,516 | B2 | 8/2017 | Ellis et al. |
| 9,951,365 | B2 | 4/2018 | Bassett et al. |
| 9,994,622 | B2 | 6/2018 | Blais et al. |
| 10,745,730 | B2 | 8/2020 | Gottesman |
| 2003/0198956 | A1 | 10/2003 | Makowski et al. |
| 2012/0259101 | A1 | 10/2012 | Tan et al. |
| 2013/0029377 | A1 | 1/2013 | Caparon et al. |
| 2014/0323691 | A1 | 10/2014 | Tan et al. |
| 2016/0222372 | A1 | 8/2016 | Walper et al. |
| 2017/0146522 | A1 | 5/2017 | Howarth |
| 2018/0327446 | A1 | 11/2018 | Fong et al. |
| 2018/0344871 | A1 | 12/2018 | Tsourkas et al. |
| 2019/0178878 | A1 | 6/2019 | Howarth |
| 2019/0309312 | A1 | 10/2019 | Ylera |
| 2020/0299358 | A1 | 9/2020 | Knappik et al. |
| 2020/0299369 | A1 | 9/2020 | Knappik |

FOREIGN PATENT DOCUMENTS

| | | |
|---|---|---|
| CN | 106967658 | 9/2020 |
| EP | 0 393 045 | 10/1990 |
| EP | 1 341 899 | 9/2003 |
| EP | 2534484 B1 | 11/2014 |
| EP | 2 993 231 | 3/2016 |
| WO | 2011098772 A1 | 8/2011 |
| WO | 2013045632 A1 | 4/2013 |
| WO | WO 2013/171156 | 11/2013 |
| WO | 2016154621 A1 | 9/2016 |
| WO | 2016183387 A1 | 11/2016 |
| WO | 2016193746 A1 | 12/2016 |
| WO | 2017058114 A1 | 4/2017 |
| WO | 2017070742 A1 | 5/2017 |
| WO | 2017112784 A1 | 6/2017 |
| WO | 2018053180 A2 | 3/2018 |
| WO | 2018189517 A1 | 10/2018 |
| WO | 2018197854 A1 | 11/2018 |
| WO | WO 2018/220386 | 12/2018 |
| WO | WO 2019/006046 | 1/2019 |

OTHER PUBLICATIONS

International Search Report and Written Opinion in International Application No. PCT/IB2020/000172, dated Jul. 27, 2020, pp. 1-18.
International Search Report and Written Opinion in International Application No. PCT/IB2020/000197, dated Aug. 28, 2020, pp. 1-18.
International Search Report and Written Opinion in International Application No. PCT/IB2020/000134, dated Aug. 27, 2020, pp. 1-18.
Brune, K. D. et al. "Plug-and-Display: decoration of Virus-Like Particles via isopeptide bonds for modular immunization" *Scientific Reports*, Jan. 19, 2016, pp. 1-13, vol. 6.
Liu, Z. et al. "A novel method for synthetic vaccine construction based on protein assembly" *Scientific Reports*, Dec. 1, 2014, pp. 1-8, vol. 4, No. 1.
Van Den Berg Can Saparoea, H. B. et al. "Display of Recombinant Proteins on Bacterial Outer Membrane Vesicles by Using Protein Ligation" *Applied and Environmental Microbiology*, Feb. 9, 2018, pp. 1-17, vol. 84, Issue 8, e02567-17.

(Continued)

*Primary Examiner* — Kagnew H Gebreyesus
(74) *Attorney, Agent, or Firm* — Saliwanchik, Lloyd & Eisenschenk

(57) ABSTRACT

Periplasmic fusion proteins comprising a binding motif attached to a C-terminus of a first protein or embedded within an amino acid sequence of the first protein, nucleic acid constructs encoding the periplasmic fusion proteins, vectors comprising the nucleic acid constructs, and methods of producing the periplasmic fusion proteins are provided. Also provided are protease deficient host cells for producing the periplasmic fusion proteins.

20 Claims, 8 Drawing Sheets

Specification includes a Sequence Listing.

(56) References Cited

OTHER PUBLICATIONS

Schmohl, L. et al. "Engineering sortase A by screening a second-generation library using phage display" *Journal of Peptide Science*, Feb. 10, 2017, pp. 631-635, Supporting Information pp. 1-14, vol. 23, Nos. 7-8.

Nguyen, H. D. et al. "Analysis and application of *Bacillus subtilis* sortases to anchor recombinant proteins on the cell wall" *AMB Express*, Jul. 21, 2011, pp. 1-11, vol. 1, No. 22.

Mazor, Y. et al. Selection of full-length IgGs by tandem disply on filamentous phage particles and *Escherichia coli* fluorescence-activated cell sorting screening *FEBS Journal*, May 26, 2010, pp. 2291-2303, vol. 277, No. 10.

Borodina, I. et al. "Disply of wasp venom allergens on the cell surface of *Saccharomyces cerevisiae*" *Microbial Cell Factories*, Sep. 24, 2010, pp. 1-13, vol. 9, No. 74.

Hatlem, D. et al. "Catching a SPY: Using the SpyCatcher-SpyTag and Related Systems for Labeling and Localizing Bacterial Proteins" *International Journal of Molecular Sciences*, Apr. 30, 2019, pp. 1-19, vol. 20, No. 9.

International Search Report and Written Opinion in International Application No. PCT/IB2019/000339, dated Sep. 13, 2019, pp. 1-22.

IMGT definitions according to Lefranc M.-P.. De RK, Tomar N. Immunoinformatics of the V, C and G domains: IMGT® definitive system for IG, TR and IgSF, MH and MhSF, Immunoinformatics: From Biology to Informatics, 2014, vol. 1184 2nd edition Springer, NY Humana Press (p. 59-107).

Abe, H., et al. "Split Spy0128 as a Potent Scaffold for Protein Cross-Linking and Immobilization." Bioconjugate Chem., 2013, vol. 24, No. 2, 242-250.

Alam, M.K et al., "Synthetic Modular Antibody Construction Using the SpyTag/SpyCatcher Protein Ligase System." ChemBioChem, 2017, vol. 18, No. 22, pp. 2217-2221.

Alam, M.K. et al., "Site-Specific Fluorescent Labeling of Antibodies and Diabodies Using SpyTag/SpyCatcher System for In Vivo Optical Imaging," Mol Imaging Biol., 2018, 13pp, https://doi.org/10.1007/s11307-018-1222-y.

Alam, M. et al., "A novel synthetic trivalent single chain variable fragment (tri-scFv) construction platform based on the SpyTag/SpyCatcher protein ligase system." BMC Biotechnology, 2018, vol. 18, No. 55, pp. 1-8.

Albrecht, H. et al. "Production of Soluble ScFvs with C-Terminal-Free Thiol for Site Specific Conjugation or Stable Dimeric ScFvs on Demand," BioconjugChem, 2004, vol. 15, No. 1, pp. 16-26.

Alves, N.J., et al. "Bacterial Nanobioreactors-Directing Enzyme Packaging into Bacterial Outer Membrane Vesicles." ACS Appl. Mater Interfaces, 2015; vol. 7, pp. 24963-24972.

Batonick, M., et al. "pMINERVA: A donor-Acceptor System for the in vivo Recombineering of scFv into IgG molecules." J Immunol Methods, 2016 vol. 431, pp. 22-30.

Berman H.M., et al. "The Protein Data Bank." Nucleic Acids Res. 2000, vol. 28, No. 1, pp. 235-242.

Brannon, J.R, 2015, "Inhibition of Outer Membrane Proteases of the Omptin Family by Aprotinin," Infect Immun., 2015, vol. 83, pp. 2300-2311.

Buldun, C.M., et al. "SnoopLigase catalyzes peptide-peptide locking and enables solid-phase conjugate isolation." J Am Chem Soc., vol. 140, No. 8, pp. 3008-3018.

Caspi, J. et al., "Distribution of split DnaE inteins in cyanobacteria," Mol Microbiol, 2003, vol. 50, No. 5, pp. 1569-1577.

Chen, W. and Georgiou, G., 2002, Cell-surface display of heterologous proteins: From high-throughput screening to environmental applications. Biotechnol Bioeng. 79:496-503.

Chichili et al., "Linkers in the structural biology of protein-protein interactions," Protein Sci., Sep. 7, 2012, vol. 22:153-167.

Cho, M.S., Establishment of a Human Somatic Hybrid Cell Line for Recombinant Protein Production. J Biomed Sci., 2002, vol. 9, pp. 631-638.

Choi, J. et al., "Protein Trans-splicing and Characterization of a Split Family B-type DNA Polymerase from the Hyperthermophilic Archaeal Parasite Nanoarchaeum equitans," J Mol. Biol., 2006,vol. 356, pp. 1093-1106.

Cloutier, S. et al., 2000, Streptabody, a high avidity molecule made by tetramerization of in vivo biotinylated, phage display-selected scFv fragments on streptavidin, Molecular Immunology, 2000, vol. 37, pp. 1067-1077.

Cuesta Angel M., et al. "Multivalent antibodies: when design surpasses evolution." Trends Biotechnol, 2010, vol. 28, pp. 355-362.

Dassa, B. et al., "Trans Protein Splicing of Cyanobacterial Split Inteins in Endogenous and Exogenous Combinations. Biochemistry," 2007, vol. 46, pp. 322-330.

Datsenko, K.A. et al.,"One-step inactivation of chromosomal genes in *Escherichia coli* K-12 using PCR products," Proc Natl Acad Sci USA, 2000, vol. 97, No. 12, pp. 6640-6645.

Ducancel F et al., "Recombinant Colorimetric Antibodies: Construction and characterization of a Bifunctional F(ab)2/Alkaline Phosphatase Conjugate Produced in *Escherichia coli*," Bio/Technol, 1993, vol. 11, pp. 601-605.

Ezkurdia I, et al, "Protein Structural Domains: Definition and Prediction," Curr Protoc Protein Sci., Supplement 66, Nov. 2011, Chapter 2:Unit2.14. doi: 10.1002/0471140864.ps0214s66, 16 pp.

Fierer, J.O., et al. "SpyLigase peptide-peptide ligation polymerizes affibodies to enhance magnetic cancer cell capture," Proc Natl Acad. Sci., 2014, vol. 111, pp. E1176-E1181.

Geller, B. L., "Antibacterial antisense," Curr. Opin. Mol. Ther., 2005, vol. 7, pp. 109-113.

Gingrich, J.C., et al. "Multiplex Detection and Quantitation of Proteins on Western Blots Using Fluorescent Probes," Biotechniques, Sep. 2000, vol. 29, No. 3, pp. 636-642.

Jia, L. et al., "Polymeric SpyCatcher scaffold enables bioconjugation in a ratio-controllable manner," Biotechnology Journal, Mar. 16, 2017, vol. 12, No. 12, doi:[10.1002/biot.201700195].

Keeble, A.H., et al., "Evolving Accelerated Amidation by SpyTag/SpyCatcher to Analyze Membrane Dynamics," Ange, Chem. Int. Ed., 2017, vol. 56, pp. 16521-16525.

Keeble, A. H., Howarth, M., 2019, Insider information on successful covalent protein coupling with help from SpyBank. Methods in Enzymology. 617: 443-461. doi.org/10.1016/bs.mie.2018.12.010.

Keeble, A.H. et al., "Approaching infinite affinity through engineering of peptide-protein interaction," Proc. Natl. Acad. Sci., 2019, vol. 116, pp. 26526-26533.

Keiler, K. et al., "Identification of Active Site Residues of the Tsp Protease," J. Biol. Chem., 1995, vol. 270, No. 48, pp. 28864-28868.

Knappik, A. et al., "Recombinant antibody Expression and Purification," In: Walker, J.M. editor. The Protein Protocols Handbook. 3rd edition. New York: Humana Press Inc., 2009, pp. 1929-1943.

Knappik, A., et al. "Development of Recombinant Human IgA for Anticardiolipin Antibodies Assay Standardization," Annals of the New York Academy of Sciences, 2009, vol. 1173, pp. 190-198.

Li et al., "Structural Analysis and Optimization of the Covalent Association between SpyCatcher and a Peptide Tag," J. Mol. Biol., 2014, vol. 426, No. 2, pp. 309-317.

Liu, X-Q et al., "Split *dnaE* Genes Encoding Multiple Novel Inteins in Trichodesmium erythraeum," J. Biol. Chem., 2003, vol. 278, pp. 26315-26318.

Mauro, V.P., "Codon Optimization in the Production of Recombinant Biotherapeutics: Potential Risks and Considerations." BioDrugs: clinical immunotherapeutics, biopharmaceuticals and gene therapy, Feb. 1, 2018, vol. 32, No. 1, pp. 69-81.

Meerman, H. et al., "Construction and Characterization of a set of *E. coli* Strains Deficient in all known Loci Affecting the Proteolytic Stability of Secreted Recombinant Proteins," Biotechnology, Nov. 1994, vol. 12, pp. 1107-1110.

Nguyen, G.K.T., et al., "Butelase 1 is an Asx-specific ligase enabling peptide macrocyclization and synthesis." Nat Chem Biol. Jul. 20, 2014, vol. 10, pp. 732-738.

Nguyen et al., et al. "Butelase-mediated cyclization and ligation of peptides and proteins," Nature protocols, 2016, vol. 11, No. 10, pp. 1977-1988.

(56) References Cited

OTHER PUBLICATIONS

Pack P, et al. "Miniantibodies: use of Amphipathic Helices to Produce Functional, Flexibly Linked Dimeric Fv Fragments with High Avidity in *Escherichia coli*," Biochemistry, 1992, vol. 31, No. 6, pp. 1579-1584.

Pack P, et al. "Tetravalent Miniantibodies with High Avidity Assembling in *Escherichia coli*." Journal of Molecular Biology, 1995, vol. 246, pp. 28-34.

Pallen, M. et al., 1997, The HtrA family of serine proteases. Mol Microbiol, 26:209-21.

Plückthun A., "Antibodies from *Escherichia coli*," Nature, Oct. 4, 1990, vol. 347, No. 6292, vol. 497-498.

Prassler, J., et al. "HuCAL Platinum, a synthetic Fab Library Optimized for Sequence Diversity and Superior Performance in Mammalian Expression Systems," J. Mol. Biol., 2011, vol. 413, No. 1, pp. 261-278.

Prouty, W.F., et al. "Effects of Protease Inhibitors on Protein Breakdown in *Escherichia coli*" J. Biol. Chem., 1972, vol. 247, pp. 3341-3352.

Qi, F. et al., "Evolutionary analysis of polyproline motifs in *Escherichia coli* reveals their regulatory role in translation," PLOS Computational Biology, Feb. 1, 2018, vol. 14, No. 2, e1005987.

Reddington, S.C., et al. "Secrets of a covalent interaction for biomaterials and biotechnology: SpyTag and SpyCatcher," Current Opinion in Chemical Biology. 2015, vol. 29, pp. 94-99.

Rheinnecker M et al. "Multivalent Antibody Fragments with High Functional Affinity for a Tumor-Associated Carbohydrate Antigen." J Immunol, 1996 vol. 157, pp. 2989-2997.

Schmohl, L., et al. "Sortase-mediated ligations for the site-specific modification of proteins," Current Opinion in Chemical Biology, 2014, vol. 22, pp. 122-128.

Shah N. et al. "Split Inteins: Nature's Protein Ligases," Israel Journal of Chemistry, 2011, vol. 5, (8-9), pp. 854-861.

Siegmund et al., "Spontaneous Isopeptide Bond Formation as a Powerful Tool for Engineering Site-Specific Antibody-Drug Conjugates," Scientific Reports, 2016, vol. 6, 39291.

Silber K. et al., "Tsp: a tail-specific protease that selectively degrades proteins with nonpolar C termini," PNAS, 1991, vol. 89, pp. 295-299.

Skerra and Plückthun,"Assembly of a Functional Immunoglobulin $F_v$ Fragment in *Escherichia coli*". Science, 1988; vol. 240, 4855, pp. 1038-1041.

Tan et al. "Kinetic Controlled Tag-Catcher Interactions for Directed Covalent Protein Assembly," Plos One, 2016, vol. 11 ,No. 10, e0165074.

Thiel, I.V., et al. "An Atypically Naturally Split Intein Engineered for Highly Efficient Protein Labeling," Angew. Chem. Int. Ed., 2014, vol. 53, pp. 1306-1310.

Toplak, et al. "Peptiligase, an Enzyme for Efficient Chemoenzymatic Peptide Synthesis and Cyclization in Water," Adv Synth Catal., 2016, vol. 358, pp. 2140-2147.

Veggiani, G. et al., "Programmable polyproteams built using twin peptide superglues," Proc. Natl. Acad. Sci., 2016, vol. 113,pp. 1202-1207.

Waugh, D.S., "Crystal structures of MBP fusion proteins," Protein Sci., Dec. 19, 2015, vol. 25, pp. 559-571.

Wu, C., et al. "Twin disulfides for orthogonal disulfide pairing and the directed folding of multicyclic peptides," Nat Chem., 2012, vol. 4, pp. 1044-1049.

Wu, H. et al., "Protein trans-splicing by a split intein encoded in a split DnaE gene of *Synechocystis* sp. PCC6803," Proc Natl Acad Sci., 1998, vol. 95, pp. 9226-9231.

Yumura, K. et al., 2017, "Use of SpyTag/SpyCatcher to construct bispecific antibodies that target two epitopes of a single antigen," J Biochem. 162(3) 203-210.

Zakeri, B. et al., "Peptide tag forming a rapid covalent bond to a protein, through engineering a bacterial adhesin," Proc Natl Acad Sci., 2012, vol. 109, pp. E690-E697.

Zettler, J. et al., "The Naturally Split Npu DnaE intein exhibits an extraordinarily high rate in the protein *trans*-splicing reaction," FEBS Letters., 2009, 553:909-914.

Chen, C. et al. "High-Level Accumulation of a Recombinant Antibody Fragment in the Periplasm of *Escherichia coli* Requires a Triple-Mutant (*degP prc spr*) Host Strain" *Biotechnology and Bioengineering*, Mar. 5, 2004, pp. 463-474, vol. 85, No. 5.

Ellis, M. et al. "Development of a High Yielding *E. coli* Periplasmic Expression System for the Production of Humanized Fab' Fragments" *Biotechnol. Prog.*, 2017, pp. 212-220, vol. 33, No. 1.

FIG. 2

SEQ ID NO: 7 Fab-His-Spy-FLAG

SEQ ID NO: 8 Fab-Spy-Sx2

SEQ ID NO: 9 Fab-FLAG-Spy-Sx2

SEQ ID NO: 10 Fab-X-Spy-Sx2

FIG. 2 (continued)

SEQ ID NO: 11 MBPΔ4aa-FLAG-SpyTag-His

SEQ ID NO: 12 MBPΔ4aa-His-SpyTag-FLAG

FIG. 6

SEQ ID NO: 33 MBP(4Δaa)-Spy-His_ST4

FIG. 8

SEQ ID NO: 34 scFv-FLAG-Spy-His

SEQ ID NO: 35 scFv(Δ6aa)-Spy-His

FIG. 9

PERIPLASMIC FUSION PROTEINS

This application claims the benefit of U.S. Provisional Application 62/819,758 filed on Mar. 18, 2019 which is hereby incorporated by reference in its entirety.

The Sequence Listing for this application is labeled "Seq-List.txt" which was created on Mar. 16, 2020 and is 27,482 bytes. The entire content of the sequence listing is incorporated hereby by reference in its entirety.

BACKGROUND

Several technologies enable covalent conjugation or ligation of polypeptides at specific pre-determined sites. One example is the SpyTag/SpyCatcher (Reddington et al., 2015) system in which the concept of spontaneous isopeptide bond formation in naturally occurring proteins has been used to covalently attach one polypeptide to another. A domain from the *Streptococcus pyogenes* protein FbaB, which contains such an isopeptide bond is split into two parts. One part, the SpyTag (SEQ ID NO: 1), is a 13 amino acid peptide that contains part (e.g., an aspartic acid residue) of the autocatalytic center. The other part, the SpyCatcher, is a 116 amino acid protein domain containing the other part (e.g., a lysine) of the center and a nearby catalytic glutamate or aspartate residue. Mixing those two polypeptides restores the autocatalytic center and leads to formation of the isopeptide bond, thereby covalently linking the SpyTag to the SpyCatcher (Zakeri et al., 2012). Further engineering has led to a shorter version of SpyCatcher with only 84 amino acids as well as an optimized version of SpyTag002 (SEQ ID NO: 2) and SpyCatcher002 with accelerated reaction (Li et al., 2014 and Keeble et al., 2017); both of which are hereby incorporated by reference in their entirety. More engineering has led to another optimized version, SpyTag003 (SEQ ID NO: 36) and SpyCatcher003, with a reaction close to the diffusion limit (Keeble et al., 2019), which is hereby incorporated by reference in entirety.

The two polypeptides to be ligated to each other are typically produced as fusion proteins with each polypeptide having a portion of the autocatalytic center from FbaB such that when the polypeptides are mixed, an isopeptide bond is formed. For example, a first polypeptide linked to SpyTag and a second polypeptide linked to SpyCatcher are produced separately as fusion proteins and when the first and second polypeptides are mixed together, an isopeptide bond is formed between SpyTag and SpyCatcher. These types of fusion proteins may be produced in bacteria. Many fusion proteins can be produced in the cytoplasm of bacteria but due to reducing conditions, disulfide-bridged proteins will not form disulfide bonds and therefore will not fold properly when expressed in the reducing environment of the cytoplasm. Many important protein classes do contain disulfide bonds, however. One example is antibody fragments. The functional expression of antibody Fv and Fab fragments was achieved by directing the transport of the expressed protein chains to the periplasm of gram-negative bacteria such as *E. coli*, which has oxidizing conditions and enables formation of disulfide bonds (Pluckthun A., 1990, Antibodies from *Escherichia coli*, Nature 347, 497-498), paving the way for the field of antibody engineering. While the bacterial recombinant expression of many SpyTag fusion proteins has been described in the literature, they were almost exclusively expressed in the bacterial cytoplasm (Keeble et al., 2019). Only a few examples exist for periplasmic bacterial expression of SpyTag fusion proteins (Alves et al., 2015; Alam et al., 2017), and the yields were either low or unclear. Keeble et al. (2019), Alves et al. (2015), and Alam et al. (2017) are hereby incorporated by reference in their entirety.

SUMMARY

Periplasmic fusion proteins comprising a binding motif (e.g., SpyTag, SpyTag002, or SpyTag003) attached to a first protein (e.g., an antigen binding fragment) or embedded within an amino acid sequence of the first protein, nucleic acid constructs encoding periplasmic fusion proteins, vectors comprising the nucleic acid constructs, and methods of producing such periplasmic fusion proteins are provided. Also provided are mutant protease deficient *E. coli* cells for producing the periplasmic fusion proteins.

In an embodiment, a periplasmic fusion protein comprises a binding motif attached to a first protein or embedded within an amino acid sequence of the first protein and the binding motif comprises SEQ ID NO: 1 or a sequence with at least 60% sequence identity to SEQ ID NO: 1. In certain embodiments, the binding motif comprises SEQ ID NO: 2 or a sequence with at least 70% sequence identity to SEQ ID NO: 2. In some embodiments, the binding motif comprises SEQ ID NO: 36 or a sequence with at least 70% sequence identity to SEQ ID NO: 36. In some embodiments, the binding motif is attached directly or via a linker sequence to an N-terminus or C-terminus of the first protein. In some embodiments, the first protein is a protein structural domain. In certain embodiments, the linker sequence comprises a purification tag. In some embodiments, the binding motif comprises SEQ ID NO: 1 or a sequence with at least 60% sequence identity to SEQ ID NO: 1 and is attached directly or via a linker sequence to the C-terminus of the first protein. In some embodiments, the binding motif is proteolytically sensitive. In some embodiments, the binding motif is proteolytically resistant. In some embodiments, the first protein is an antigen binding fragment. In some embodiments, the first protein is an antigen binding fragment and the antigen binding fragment is Fab, scFv, or scFab. In some embodiments, the antigen binding fragment is Fab. In certain embodiments, the periplasmic fusion protein further comprises a purification tag attached to an N-terminus or a C-terminus of the binding motif. In certain embodiments, the binding motif is a linker sequence linking a C-terminus of the first protein to an N-terminus of a second protein or the N-terminus of the first protein to the C-terminus of the second protein.

Nucleic acid constructs comprising a polynucleotide sequence encoding the periplasmic fusion proteins are also provided. Also provided are vectors comprising the nucleic acid constructs.

Methods are also provided for producing a periplasmic fusion protein comprising a binding motif attached to a first protein or embedded within an amino acid sequence of the first protein and the binding motif comprises SEQ ID NO: 1 or a sequence with at least 60% sequence identity to SEQ ID NO: 1, the binding motif comprises SEQ ID NO: 2 or a sequence with at least 70% sequence identity to SEQ ID NO: 2, or the binding motif comprises SEQ ID NO: 36 or a sequence with at least 70% sequence identity to SEQ ID NO: 36. In some embodiments, the method comprises culturing *E. coli* host cells transformed with a vector containing nucleic acid encoding the periplasmic fusion protein in a culture medium under conditions effective to express the periplasmic fusion protein and recovering the periplasmic fusion protein from the *E. coli* host cells. In some embodiments, the binding motif of the fusion protein expressed in the *E. coli* host cells is proteolytically resistant. In certain embodiments, the binding motif of the fusion protein expressed in the *E. coli* host cells is proteolytically sensitive. In such embodiments, the *E. coli* host cells are mutant cells deficient in one or more periplasmic proteases. In some embodiments, the mutant *E. coli* cells used in the method are deficient in functional chromosomal gene tsp encoding protease Tsp (tail-specific protease). In some embodiments, the mutant *E. coli* cells used in the method are deficient in functional chromosomal genes tsp and ompT encoding proteases Tsp and OmpT (outer membrane protein T), respectively.

Also provided is an *E. coli* TG1, TG1 F-, XL1 Blue, MC1061, SS320, BL21, JM83, JM109, HB2151, W3110, or Cmax5 alpha strain deficient in functional chromosomal gene tsp encoding protease Tsp. In some embodiments, such mutant *E. coli* strains comprise a nucleic acid encoding a periplasmic fusion protein comprising a binding motif and the binding motif comprises SEQ ID NO: 1 or a sequence with at least 60% sequence identity to SEQ ID NO: 1. Also provided is an *E. coli* TG1, TG1 F-, XL1 Blue, MC1061, SS320, BL21, JM83, JM109, HB2151, W3110, or Cmax5 alpha strain deficient in functional chromosomal genes tsp and ompT encoding proteases Tsp and ompT, respectively. In some embodiments, such mutant *E. coli* strains comprise a nucleic acid encoding a periplasmic fusion protein comprising a binding motif and the binding motif comprises SEQ ID NO: 2 or a sequence with at least 70% sequence identity to SEQ ID NO: 2. In certain embodiments, such mutant *E. coli* strains comprise a nucleic acid encoding a periplasmic fusion protein comprising a binding motif and the binding motif comprises SEQ ID NO: 36 or a sequence with at least 70% sequence identity to SEQ ID NO: 36.

BRIEF DESCRIPTION OF THE DRAWINGS

FIG. 2 illustrates the partial nucleotide and amino acid sequences of Fab-SpyTag constructs used in periplasmic expression studies as described in Example 1. CH1: Last 7 amino acid residues of human IgG1 CH1 domain. Hinge: First 4 amino acid residues of human IgG1 hinge domain. EcoRI Linker: 2 amino acids introduced by restriction site. Linker: short 1-4 amino acid residue linker sequences. SpyTag (Spy): sequence AHIVMVDAYKPTK. His-tag: six histidine residues. X Linker: (GGGS)$_2$ Linker. Flag: sequence DYKDDDDK. Sx2 tag: two Strep-Tags (SAWSHPQFEK) joined by a linker.

FIG. 6 illustrates the partial nucleotide and amino acid sequences of Fab-SpyTag002 constructs used in studies of mutant *E. coli* TG1 F- strains as described in Example 8. CH1: Last 7 amino acid residues of human IgG1 CH1 domain. Hinge: First 4 amino acid residues of human IgG1 hinge domain. EcoRI Linker: 2 amino acids introduced by restriction site. Linker: short 1-4 amino acid residue linker sequences. SpyTag002 (Spy002): sequence VPTIVMVDAYKRYK. His-tag: six histidine residues. X Linker: (GGGS)$_2$ Linker. Flag: sequence DYKDDDDK.

FIG. 8 illustrates the partial nucleotide and amino acid sequences of MBP-SpyTag constructs used in periplasmic expression studies as described in Examples 2, 6, and 10.

FIG. 9 illustrates the partial nucleotide and amino acid sequences of scFv-SpyTag constructs used in periplasmic expression studies as described in Examples 3, 7, and 11.

DETAILED DESCRIPTION

Figure 1:
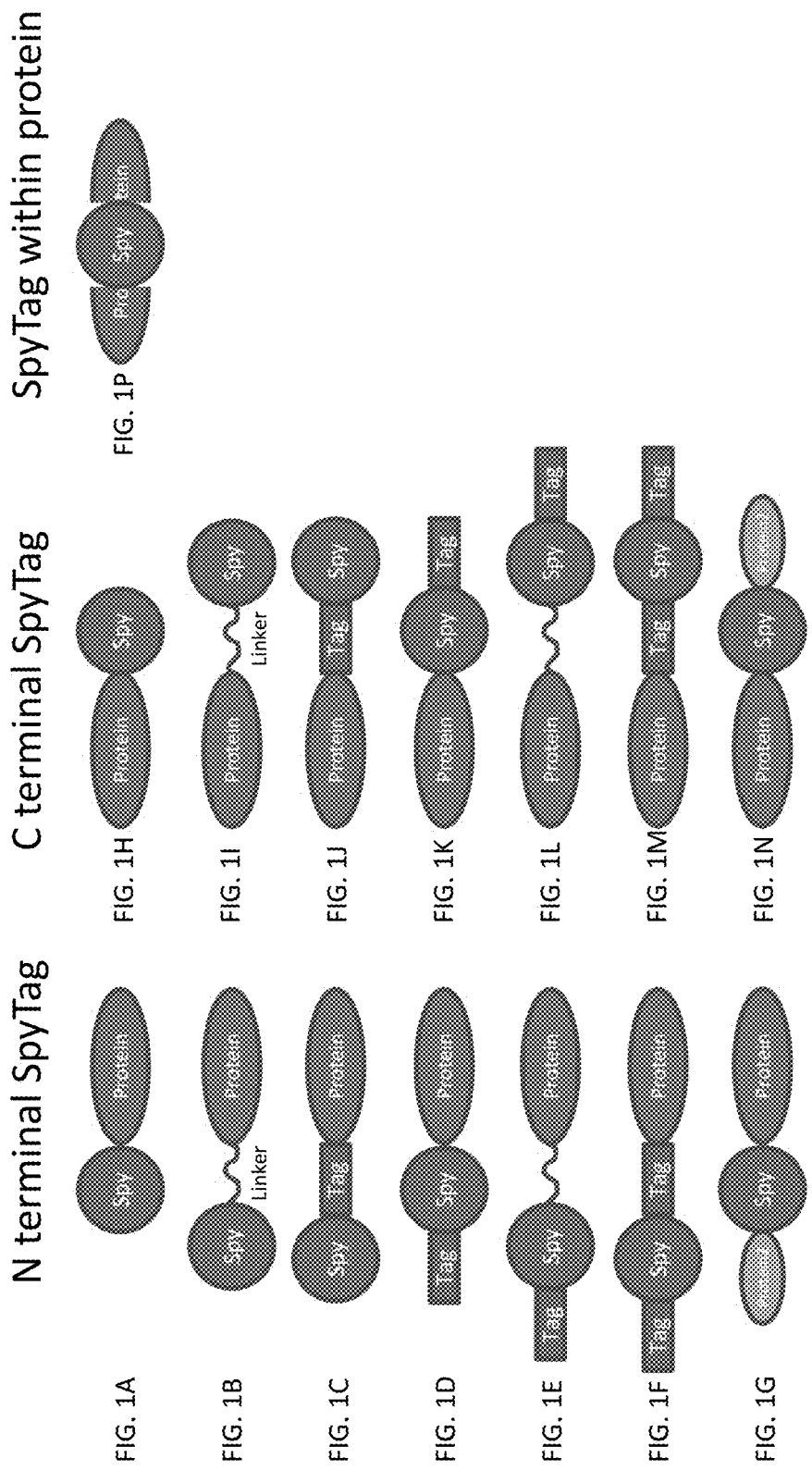
FIGS. 1A, 1B, 1C, 1D, 1E, 1F, 1G, 1H, 1I, 1J, 1K, 1L, 1M, 1N, and 1P illustrate various periplasmic fusion protein constructs according to embodiments.

Periplasmic fusion proteins comprising a binding motif (i.e., SpyTag, SpyTag002, or SpyTag003) attached to a first protein (e.g., an antigen binding fragment or a protein structural domain) or embedded within an amino acid sequence of the first protein, nucleic acid constructs encoding the periplasmic fusion proteins, vectors comprising the nucleic acid constructs, and methods of producing the periplasmic fusion proteins are provided. Also provided are protease deficient host cells for producing the periplasmic fusion proteins.

It has been discovered that fusion proteins comprising SpyTag, SpyTag002, or SpyTag003 binding motifs are digested by periplasmic proteases when periplasmically expressed in *E. coli*. Linking SpyTag directly to a C-terminus or N-terminus of a protein, protein structural domain, or protein structural domain fragment without a linker sequence results in a fusion protein in which the SpyTag is substantially resistant to periplasmic proteases while being produced in *E. coli*. It has also been discovered that when SpyTag, SpyTag002, or SpyTag003 is linked with a linker sequence to an N- or C-terminus of a protein or protein domain, the SpyTag, SpyTag002, or SpyTag003 is sensitive to periplasmic proteases during expression of the fusion protein in bacteria. For such protease sensitive fusion proteins, *E. coli* host cells have been created that are deficient in periplasmic proteases responsible for SpyTag, SpyTag002, or SpyTag003 cleavage.

Definitions

Unless otherwise stated, the following terms used in this application, including the specification and claims, have the definitions given below. As used in this specification and the appended claims, the singular forms "a", "an", and "the" include plural referents unless the content clearly dictates otherwise.

"Antibody" refers to an immunoglobulin, composite (e.g., fusion), or fragmentary form thereof. The term includes but is not limited to polyclonal or monoclonal antibodies of the classes IgA, IgD, IgE, IgG, and IgM, derived from antibody-producing cell lines or from in vitro antibody libraries, including natural or genetically modified or synthetic forms such as humanized, human, single-chain, chimeric, synthetic, recombinant, hybrid, mutated, grafted, and other in vitro generated antibodies. "Antibody" also includes composite forms including but not limited to fusion proteins having an immunoglobulin moiety.

As used herein, the phrase "antigen binding fragment" refers to proteins comprising the antigen binding portion of an antibody, such as an Fab. Other antigen binding fragments include variable fragments (Fv), disulfide-stabilized Fv fragments (dsFv), single chain variable fragments (scFv) or single chain Fab fragments (scFab). Further examples of antigen binding fragments include monovalent forms of antigen binding fragments that contain the antigen binding site including variable domain of heavy chain antibodies (VHH), single domain antibodies (sdAbs), or Shark Variable New Antigen Receptors (VNAR). Furthermore, non-antibody scaffolds such as Variable Lymphocyte Receptors (VLRs), affimers, affibodies, darpins, anticalins, monobodies, or antigen-binding peptides can also be considered an "antigen binding fragment".

The term "binding motif" refers to a protein sequence that is attached to polypeptides and that enables the formation of a covalent linkage to another polypeptide. Non-limiting examples of binding motifs include SpyTag, SpyTag002, and SpyTag003 sequences. SpyTag sequences form a covalent linkage with SpyCatcher sequences. The binding motifs may be fused to an N-terminus, a C-terminus, or may be embedded within the amino acid sequence of the polypeptide. One or more linker sequences (e.g., a glycine/serine rich linker) or one or more protein tags may flank the binding motifs to enhance accessibility for reaction, to enhance flexibility of the fused polypeptides or for purification and/or detection of the polypeptide. Where a binding motif connects two or more proteins, the N- and C-terminus of the binding motif may be flanked by one or more linker sequences to enhance accessibility for reaction, to enhance flexibility of the fused polypeptides or for purification and/or detection of the polypeptide.

The term "prokaryotic system" refers to prokaryotic cells such as bacterial cells (e.g., bacterial cells having the genus *Escherichia* or *Salmonella*) or prokaryotic phages or bacterial spores. The term "eukaryotic system" refers to eukaryotic cells including cells of animal, plants, fungi and protists, and eukaryotic viruses such as retrovirus, adenovirus, baculovirus. Prokaryotic and eukaryotic systems may be, collectively, referred to as "expression systems".

The term "expression cassette" is used here to refer to a functional unit that is built in a vector for the purpose of expressing recombinant polypeptides in the periplasm. An expression cassette includes a promoter or promoters, a transcription terminator sequence, a ribosome binding site or sites, and the DNA encoding the fusion proteins. Other genetic components can be added to an expression cassette, depending on the expression system (e.g., enhancers and polyadenylation signals for eukaryotic expression systems).

As used herein the term "vector" refers to a nucleic acid molecule, preferably self-replicating within a cell, which transfers an inserted nucleic acid molecule into and/or between host cells. Typically vectors are circular DNA comprising a replication origin, a selection marker, and/or viral package signal, and other regulatory elements. Vector, vector DNA, plasmid DNA, phagemid DNA are interchangeable terms in description of this invention. The term includes vectors that function primarily for insertion of DNA or RNA into a cell, replication vectors that function primarily for the replication of DNA or RNA, and expression vectors that function for transcription and/or translation of the DNA or RNA. Also included are vectors that provide more than one of the above functions.

As used herein the term "expression vector" is a polynucleotide which, when introduced into an appropriate host cell, leads under appropriate conditions to the transcription and translation of one or more polypeptides. The term "expression vector", refers to vectors that direct the expression of polypeptides of interest fused in frame with a binding motif.

As used herein the terms "nucleic acids" and "polynucleotides" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the nucleotide polymer.

As used herein the term "amino acid" refers to either natural and/or unnatural or synthetic amino acids, both the D or L optical isomers, amino acid analogs, and peptidomimetics.

As used herein the terms "polypeptide", "peptide", and "protein," are used interchangeably herein to refer to polymers of amino acids of any length.

As used herein the term "protein structural domain" or "domain" refers to a semiautonomous, compact folding unit with a separate hydrophobic core" (Ezkurdia and Tress, 2011). The domain is a conserved part of a given protein sequence and structure that can evolve, function, and exist independently of the rest of the protein chain. Each domain forms a compact three-dimensional structure that can be independently stable and folded. Examples of protein structural domains include, but are not limited to, the constant domain (e.g., CH1 including the first two amino acids of the hinge region) of human IgG1 and maltose binding protein (MBP). The "C-terminus" of a protein structural domain refers to the last amino acid that is annotated as structured (i.e. visible in crystal structure) in the protein data bank (Berman et al, 2000) in a crystal structure of the same or of a closely related protein structural domain (i.e., having at least 70% sequence identity). Protein structural domains can be shortened by up to ten amino acids (e.g., 1, 2, 3, 4, 5, 6, 7, 8, 9, or 10) on the N or C terminus without losing their ability to fold and, hence, their ability to remain structural domains.

As used herein the term "host cell" includes an individual cell or cell culture which can be, or has been, a recipient for the disclosed expression constructs. Host cells include progeny of a single host cell. The progeny may not necessarily be completely identical to the original parent cell due to natural, accidental, or deliberate mutation.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region or the entire designated sequence if a region is not specified), when compared and aligned for maximum correspondence over a comparison window.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, about 10 to about 300, about 10 to about 150 in which a sequence may be compared to a reference sequence of the same number of contiguous positions after the two sequences are optimally aligned. The comparison window can also be the entire length of either the reference or the test sequence.

Percent sequence identity and sequence similarity can be determined using the BLAST 2.0 algorithm, which is described in Altschul et al. (J. Mol. Biol. 215:403-10, 1990). Software for performing BLAST 2.0 analyses is publicly available through the National Center for Biotechnology Information (Worldwide Web site: ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Periplasmic Fusion Proteins

In an embodiment, a periplasmic fusion protein comprises a binding motif (e.g., SpyTag, SpyTag002, or SpyTag003) attached to a first protein (FIGS. 1A-1N) or embedded within an amino acid sequence (e.g., FIG. 1P) of the first protein. As used herein, a "periplasmic fusion protein" refers to a protein produced in the periplasm of a suitable bacterial host cell and comprises two polypeptides, the first one being any protein and the second being a SpyTag, SpyTag002, or SpyTag003 binding motif. The binding motif can be attached directly (FIGS. 1A, 1D, 1G, 1H, 1K, 1N) or via a linker sequence (FIGS. 1B, 1C, 1E, 1F, 1I, 1J, 1L, 1M) to an N-terminus or a C-terminus of the first protein. In certain embodiments, the first protein is a protein structural domain. In some embodiments, the first protein is an antigen binding fragment (e.g., Fab, scFv, or scFab). As used herein, a "binding motif" refers to a peptide sequence that is attached to a protein expressed in the periplasm and that facilitates the formation of a covalent linkage via protein ligation to another binding motif (e.g., SpyCatcher, SpyCatcher002, or SpyCatcher003) attached to another polypeptide when the two binding motifs are brought into contact with one another. The covalent bond between the two binding motifs is formed either spontaneously or with the help of an enzyme. For example, the binding motif can form a covalent bond with another binding motif on the N-terminus of an Fc fragment or with a multimerized binding motif. An example of an Fc fragment having another binding motif is described in co-pending U.S. application 62/819,748 (Antigen Binding Fragments Conjugated to a Plurality of Fc Isotypes and Subclasses; filed Mar. 18, 2019; BRL.123P) and an example of a multimerized binding motif is described in co-pending U.S. application 62/819,753 (Antigen Binding Proteins, filed Mar. 18, 2019; BRL.129P), each of which is incorporated herein in its entirety. In some embodiments, the binding motif comprises SEQ ID NO: 1 (i.e., SpyTag) or a sequence with at least 60% sequence identity to SEQ ID NO: 1. In some embodiments, the binding motif comprises SEQ ID NO: 2 (i.e., SpyTag002) or a sequence with at least 70% sequence identity to SEQ ID NO: 2. In certain embodiments, the binding motif comprises SEQ ID NO: 36 (i.e., SpyTag003) or a sequence with at least 78% sequence identity to SEQ ID NO: 36.

In some instances, attaching the binding motif (e.g., SpyTag) directly to the first protein (i.e., without a linker sequence; FIGS. 1A, 1D, 1G, 1H, 1K, 1N) results in a periplasmic fusion protein that is substantially proteolytically insensitive, i.e., is resistant to cleavage by a periplasmic protease during expression.

In some embodiments, the periplasmic fusion protein comprises at least one linker sequence between the first protein and the binding motif. As used herein, a "linker sequence" or "linker" refers to a peptide or polypeptide containing one or more amino acid residues (e.g., 1, 2, 3, 4, 5, 10 or more amino acid residues) joined by a peptide bond(s). Such linkers can provide rotational freedom that allows each component of the fusion protein to interact with its intended target without hindrance. These linkers can be mixtures of glycine and serine, such as -(GGGS)$_n$-, where n is 1, 2, 3, 4, or 5. Other suitable peptide/polypeptide linker sequences optionally include naturally occurring or non-naturally occurring peptides or polypeptides. Optionally, the peptide or polypeptide linker sequences are flexible peptides or polypeptides (FIGS. 1B, 1E, 1I, 1L). Exemplary flexible peptides/polypeptides include, but are not limited to, the amino acid sequences Gly-Ser, Gly-Ser-Gly-Ser, Ala-Ser, Gly-Gly-Gly-Ser, Gly$_4$-Ser, (Gly$_4$-Ser)$_2$, (Gly$_4$-Ser)$_3$, (Gly$_4$-Ser)$_4$, (Gly$_4$-Ser)$_2$-Gly-Ala-Gly-Ser-Gly$_4$-Ser, Gly-(Gly$_4$-Ser)$_2$, Gly$_4$-Ser-Gly, Gly-Ser-Gly$_2$ and Gly-Ser-Gly$_n$-Ser. Other suitable peptide linker sequences optionally include the TEV linker ENLYFQG, a linear epitope recognized by the Tobacco Etch virus protease. Exemplary peptides/polypeptides include, but are not limited to, GSENLYFQGSG. Other suitable peptide linker sequences include helix forming linkers such as Ala-(Glu-Ala-Ala-Ala-Lys)$_n$-Ala (n=1-5). In some embodiments, the linker sequence is a GAP (Gly Ala Pro) sequence. In some embodiments, the linker sequence comprises a purification tag (FIGS. 1C, 1F, 1J, 1M). Purification tags can include, but are not limited to, polyhistidine or His-tag and FLAG®-tag (i.e., amino acid sequence DYKDDDDK where D is aspartic acid, Y is tyrosine, and K is lysine). In certain embodiments, the linker sequence comprises the binding motif (FIGS. G and N) and optionally comprises a purification tag and/or a flexible linker sequence attached to either or both a C- and N-terminus of the binding motif. In some embodiments, a sequence of 1 to 50 amino acid residues can be used as a linker. In some embodiments, the linkers are protease resistant (i.e., periplasmic expression of a polypeptide having the linker in a host cell occurs without cleavage of the linker by a protease). Where two or more linker sequences are used between a protein and the binding motif, the two or more linker sequences can be the same or different.

In some embodiments in which the periplasmic fusion protein comprises a linker sequence between the first protein and the binding motif, the binding motif (i.e., SpyTag, SpyTag002, and SpyTag003) may be proteolytically sensitive, i.e., the binding motif can be cleaved by one or more E. coli proteases during periplasmic expression. In certain embodiments, cleavage of the binding motif by periplasmic proteases is dependent on the linker length (i.e., number of amino acids) but independent of the linker amino acid composition.

In some embodiments, the linker sequence comprises SpyTag, SpyTag002, or SpyTag003 binding motif. In this embodiment, the binding motif links an N-terminus of the first protein to a C-terminus of a second protein (FIG. 1G) or the C-terminus of the first protein to the N-terminus of the second protein (FIG. 1N). Examples of a second protein include, but are not limited to, an antigen binding fragment, a fluorescent protein such as green fluorescent protein, an enzyme such as horse radish peroxidase or other peroxidases, alkaline phosphatase, luciferase, split fluorescent protein, and MBP. In certain embodiments, the linker sequence comprising SpyTag, SpyTag002, or SpyTag003 further comprises a purification tag or flexible linker sequence between the binding motif and either or both of the first and second proteins.

In certain embodiments, the periplasmic fusion protein has a purification tag attached to the N-terminus of the binding motif (FIGS. 1D, 1E), to the C-terminus of the binding motif (FIGS. 1K, 1L) or to both the N- and C-termini of the binding motif (FIGS. 1F and 1M).

Nucleic Acid Constructs

Also provided are nucleic acid constructs that encode for a periplasmic fusion protein, without or with a linker between the first protein and the binding motif and/or between the binding motif and the second protein of the periplasmic fusion protein. Such nucleic acids can be present in an expression vector in an appropriate prokaryotic host cell.

Typically, a polynucleotide sequence encoding a Fab fused at the C-terminus to a binding motif encodes two peptides, namely, the L and H chain of the Fab. A binding motif, such as a SpyTag, can be fused to either L or H chain, either directly or via one or more linkers. A Fab expression cassette can comprise a bicistronic vector that produces one mRNA encoding both L and H chains, at least one of which is fused to a binding motif. Also, both of H and L chains can have a signal peptide to direct their export into the periplasm.

The nucleic acid constructs are typically introduced into various vectors. The vectors described herein generally comprise transcriptional or translational control sequences required for expressing the fusion proteins. Suitable transcription or translational control sequences include, but are not limited to, replication origin, promoter, enhancer, repressor binding regions, transcription initiation sites, ribosome binding sites, translation initiation sites, and termination sites for transcription and translation.

The origin of replication (generally referred to as an ori sequence) permits replication of the vector in a suitable host cell. The choice of ori will depend on the type of host cells and/or genetic packages that are employed. Where the host cells are prokaryotes, the expression vector typically comprises ori sequences directing autonomous replication of the vector within the prokaryotic cells. Preferred prokaryotic ori is capable of directing vector replication in bacterial cells. Non-limiting examples of this class of ori include pMB1, pUC, as well as other E. coli origins.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase.

The choice of promoters will largely depend on the host cells in which the vector is introduced. For prokaryotic cells, a variety of robust promoters are known in the art. Preferred promoters are lac promoter, Trc promoter, T7 promoter and pBAD promoter.

In constructing the subject vectors, the termination sequences associated with the protein coding sequence can also be inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional readthrough. Preferred terminator sequences (or termination sites) of the present invention have a gene that is followed by a transcription termination sequence, either its own termination sequence or a heterologous termination sequence. Examples of such termination sequences include stop codons coupled to various yeast transcriptional termination sequences or mammalian polyadenylation sequences that are known in the art and are widely available. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, zeocin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In one embodiment, the expression vector is a shuttle vector, capable of replicating in at least two unrelated host systems. In order to facilitate such replication, the vector generally contains at least two origins of replication, one effective in each host system. Typically, shuttle vectors are capable of replicating in a eukaryotic host system and a prokaryotic host system. This enables detection of protein expression in the eukaryotic host (the expression cell type) and amplification of the vector in the prokaryotic host (the amplification cell type). Preferably, one origin of replication is derived from SV40 or 2u and one is derived from pUC, although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized.

The vectors encompassed by the invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or sequence data in the public or proprietary databases to obtain a desired vector by any synthetic means available in the art. Additionally, using well-known restriction and ligation techniques, appropriate sequences can be excised from various DNA sources and integrated in operative relationship with the exogenous sequences to be expressed in accordance with embodiments described herein.

Methods of Producing Fusion Proteins

Also provided are methods for producing a periplasmic fusion protein comprising a binding motif attached, optionally via one or more linker, to a first protein or to a first and second protein. In an embodiment, the method comprises culturing E. coli host cells transformed with a vector containing nucleic acid encoding the periplasmic fusion protein in a culture medium under conditions effective to express the periplasmic fusion protein in the host cells. Any suitable strain of E. coli can be used to produce the periplasmic fusion protein. One such strain of E. coli that can be used for protein (e.g., antibody, antibody fragment, or MBP) expression is the TG1 strain. TG1 strain is based on Escherichia coli K-12(genotype glnV44 thi-1 Δ(lac-proAB) Δ(mcrB-hsdSM)5($r_K$-$m_K$-) F' [traD36 proAB+ lacIq lacZΔM15]), which is commonly used for expression of antibody and antibody fragments in the periplasm (see Knappik 2009, for example, for experiments showing periplasmic expression). In some embodiments, the E. coli host cell strain is TG1 F- (genotype glnV44 thi-1 Δ(lac-proAB) Δ(mcrB-hsdSM)5($r_K$-$m_K$-)), which is an F pilus depleted form. In certain embodiments, the E. coli host cell strain includes, but is not limited to, XL1 Blue, MC1061, SS320, BL21, JM83, JM109, HB2151, W3110, Cmax5 alpha and any E. coli strains suitable for functional expression of antibody fragments in E. coli. In some embodiments, the E. coli host cells are mutant cells deficient in one or more periplasmic proteases. In some embodiments, the mutant E. coli cells are deficient in functional chromosomal gene tsp encoding protease Tsp (tail-specific protease). In some embodiments, the mutant E. coli cells are deficient in functional chromosomal genes tsp and ompT encoding proteases Tsp and OmpT (outer membrane protein T), respectively. The gene(s) for the protease(s) can be "knocked out", for example, by deleting or replacing the gene(s) with a foreign DNA sequence, such as a gene encoding antibiotic resistance. One such process of knocking out a protease gene is described by Datsenko and Wanner (2000), *Proc Natl Acad Sci USA*, 97 (12): 6640-6645. In some embodiments the gene(s) for the protease(s) are modified to produce a mutated protease with no or reduced proteolytic activity (Keiler, 1995). In some embodiments, the expression of tsp or ompT protease(s) is inhibited by antisense morpholinos, antisense peptide nucleic acids, or other antisense nucleotide oligomers (Geller, 2005) leading to reduced or eliminated tsp or ompT protease activity, respectively, within E. coli. In some embodiments both tsp and ompT proteases are inhibited by antisense morpholinos, antisense peptide nucleic acids, or other antisense nucleotide oligomers leading to reduced or eliminated tsp and ompT protease activity. In some embodiments tsp or ompT protease activity is reduced or eliminated by chemical protease inhibitors including, but not limited to, phenylmethane sulfonyl fluoride or p-toluenesulfonyl fluoride (Prouty and Goldberg, 1972), by peptides or small proteins such as aprotinin (Brannon, 2015), or metal cations (Silber, 1991). In some embodiments both tsp and ompT protease activities are reduced or eliminated by chemical inhibitors as described above.

Mutant E. coli TG1 F- strain SK4 (DSM 33004) and SK13 (DSM 33005) were deposited with the Leibniz Institute DSMZ-German Collection of Microorganisms and Cell Cultures, Inhoffenstraße 7B, 38124 Braunschweig, Germany on Jan. 8, 2019. Mutant E. coli TG1 F- strain SK4 having DSMZ accession number DSM 33004 is deficient in tsp and mutant E. coli TG1 F- strain SK13 having DSMZ accession number DSM 33005 is deficient in both tsp and ompT.

A vector containing a nucleic acid encoding the periplasmic fusion protein can be transformed into a cell using standard techniques, for example, by employing chemical methods (Green R, Rogers E J. Transformation of chemically competent *E. coli*. Methods Enzymol 2013; 529:329-36) or by electroporation. In some embodiments in which the binding motif is SEQ ID NO: 1 (SpyTag), the periplasmic fusion protein is transformed into mutant *E. coli* TG1 F- strain having DSMZ accession number DSM 33004, which is deficient in tsp. In some embodiments in which the binding motif is SEQ ID NO: 2 (SpyTag002) or SEQ ID NO: 36 (SpyTag003), the periplasmic fusion protein is transformed into mutant *E. coli* TG1 F- strain having DSMZ accession number DSM 33005, which is deficient in tsp and ompT.

Cells able to express the one or more markers are able to survive/grow/multiply under certain artificially imposed conditions, for example the addition of a toxin or antibiotic to the culture medium, because of the properties endowed by the polypeptide/gene or polypeptide component of the selection system incorporated therein (e.g., antibiotic resistance). Those cells that cannot express the one or more markers are not able to survive/grow/multiply in the artificially imposed conditions.

Any suitable selection system may be employed in the method described herein. Typically the selection system may be based on including in the vector one or more genes that provides resistance to a known antibiotic, for example a tetracycline, chloramphenicol, kanamycin or ampicillin resistance gene. Cells that grow in the presence of a relevant antibiotic can be selected as they express both the gene that gives resistance to the antibiotic and the desired protein.

In an embodiment, the method further comprises the step of culturing the transformed cell in a medium to thereby express the periplasmic fusion protein.

The method can also use an inducible expression system or a constitutive promoter to express the periplasmic fusion protein.

Any suitable medium may be used to culture the transformed cell. The medium may be adapted for a specific selection system, for example the medium may comprise an antibiotic, to allow only those cells which have been successfully transformed to grow in the medium.

The expressed fusion protein is then recovered from the periplasm of the host cells by first lysing the bacteria either by whole cell lysis or by periplasmic lysis. The method can further comprise one or more steps to extract and purify the periplasmic fusion protein. The periplasmic fusion protein can be separated from the cell extract by suitable purification procedures including, but not limited to, protein A chromatography, protein L chromatography, thiophilic, mixed mode resins, nickel nitrilotriacetic acid (Ni-NTA) resin for His-tag, Strep-Tactin® or Strep-Tactin® XT resin for Strep-tag®, FLAG®-tag, hydroxyapatite chromatography, gel electrophoresis, dialysis, ammonium sulphate, ethanol or PEG fractionation/precipitation, ion exchange membranes, expanded bed adsorption chromatography, or simulated moving bed chromatography.

In some embodiments, the method further comprises measuring the quantity of expression of the periplasmic fusion protein after purification.

Additional Disclosure and Claimable Subject Matter

Item 1. A periplasmic fusion protein comprising a binding motif attached to a first protein or embedded within an amino acid sequence of the first protein, wherein the binding motif comprises SEQ ID NO: 1 or a sequence with at least 60% sequence identity to SEQ ID NO: 1.

Item 2. The periplasmic fusion protein of item 1, wherein the binding motif is attached directly or via a linker sequence to the N terminus of the first protein.

Item 3. The periplasmic fusion protein of item 1, wherein the binding motif is attached directly or via a linker sequence to the C terminus of the first protein.

Item 4. The periplasmic fusion protein of item -2 or 3, wherein the linker sequence comprises a purification tag.

Item 5. The periplasmic fusion protein of item 3, wherein the binding motif is attached directly to the C-terminus of a protein structural domain in the first protein and the binding motif is proteolytically resistant.

Item 6. The periplasmic fusion protein of item 5, wherein the protein structural domain is a human scFv single chain antibody fragment that is C-terminally truncated within the FR4 region.

Item 7. The periplasmic fusion protein of item 3, wherein the binding motif is attached to the C-terminus of the protein structural domain in the first protein via a 1 or 2 amino acid linker.

Item 8. The periplasmic fusion protein of any one of items 3, wherein the binding motif is attached to the C-terminus at IMGT position 121 of a human heavy chain CH1 antibody domain via a 2, 3, or 4 amino acid linker.

Item 9. The periplasmic fusion protein of item 3, wherein the binding motif is attached to the C-terminus at IMGT position 121 of a human constant light chain antibody domain via a 2, 3, or 4 amino acid linker.

Item 10. The periplasmic fusion protein of any one of items 1-9, further comprising a purification tag attached to an N-terminus or a C-terminus of the binding motif.

Item 11. The periplasmic fusion protein of any one of items 1-10, wherein the binding motif links the C-terminus of the first protein to the N-terminus of a second protein or the N-terminus of the first protein to the C-terminus of the second protein.

Item 12. A nucleic acid construct comprising a polynucleotide sequence encoding the periplasmic fusion protein as defined in any one of items 1-11.

Item 13. A vector comprising the nucleic acid construct of item 12.

Item 14. A method for producing a periplasmic fusion protein, the method comprising: culturing *E. coli* host cells transformed with a vector containing nucleic acid encoding the periplasmic fusion protein in a culture medium under conditions effective to express the periplasmic fusion protein, wherein:

the periplasmic fusion protein comprises a binding motif attached to a first protein or embedded within an amino acid sequence of the first protein;

the binding motif comprises SEQ ID NO: 1 or a sequence with at least 60% sequence identity to SEQ ID NO: 1; and the *E. coli* host cells have reduced or no Tsp protein activity as compared to a wild-type cell resulting from:

a) a mutation in the Tsp gene that encodes a mutated Tsp protein and the mutation reduces or eliminates protease activity; or b) a mutation in the Tsp gene or regulatory sequence of the Tsp gene that reduces or eliminates expression of the Tsp protein; or c) one or more deletions of regions in the bacterial chromosome that reduces or eliminates Tsp protein activity; or d) an inhibitor or inactivator that reduces or eliminates Tsp protease activity or an inhibitor of Tsp protease expression; and recovering the periplasmic fusion protein from the *E. coli* host cells.

Item 15. A method for producing a periplasmic fusion protein, the method comprising:

culturing *E. coli* host cells transformed with a vector containing nucleic acid encoding the periplasmic fusion protein in a culture medium under conditions effective to express the periplasmic fusion protein, wherein:

the periplasmic fusion protein comprises a binding motif attached to a first protein or embedded within an amino acid sequence of the first protein;

the binding motif comprises SEQ ID NO: 2 or a sequence with at least 70% sequence identity to SEQ ID NO: 2 or SEQ ID NO: 36 or a sequence with at least 78% sequence identity to SEQ ID NO: 36; and the *E. coli* host cells have reduced or no Tsp protein activity and ompT protein activity as compared to a wild-type cell resulting from:

a) a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity; and b) a mutation in the ompT gene that encodes a mutated ompT protein and the mutation reduces or eliminates protease activity, or a mutation in the ompT gene or regulatory sequence of the ompT gene that reduces or eliminates expression of the ompT protein, or one or more deletions of regions in the bacterial chromosome that reduces or eliminates ompT protein activity; and recovering the periplasmic fusion protein from the *E. coli* host cells.

Item 16. A method for producing a periplasmic fusion protein, the method comprising:
culturing *E. coli* host cells transformed with a vector containing nucleic acid encoding the periplasmic fusion protein in a culture medium under conditions effective to express the periplasmic fusion protein, wherein:
  the periplasmic fusion protein comprises a binding motif attached to a first protein or embedded within an amino acid sequence of the first protein;
  the binding motif comprises SEQ ID NO: 2 or a sequence with at least 70% sequence identity to SEQ ID NO: 2 or SEQ ID NO: 36 or a sequence with at least 78% sequence identity to SEQ ID NO: 36; and
  the *E. coli* host cells have reduced or no Tsp protease activity and ompT protease activity as compared to a wild-type cell resulting from:
  a) an inhibitor or inactivator of Tsp protease or an inhibitor of Tsp expression; and
  b) an inhibitor or inactivator of ompT protease or an inhibitor of ompT expression; and
  recovering the periplasmic fusion protein from the *E. coli* host cells.

Item 17. The method of any one of items 14-16, wherein the binding motif is attached directly or via a linker sequence to the N terminus of the first protein.

Item 18. The method of any one of items 14-16, wherein the binding motif is attached directly or via a linker sequence to the C terminus of the first protein.

Item 19. The method of any one of items 14-18, wherein the first protein is a protein structural domain.

Item 20. The method of any one of items 17-19, wherein the linker sequence comprises a purification tag.

Item 21. The method of item 18, wherein the binding motif comprises the amino acid sequence as set forth in SEQ ID NO: 1 or a sequence with at least 60% sequence identity to SEQ ID NO: 1 and is attached directly to the C-terminus of the first protein.

Item 22. The method of any one of items 14-21, wherein the binding motif is proteolytically sensitive.

Item 23. The method of any one of items 14-21, wherein the binding motif is proteolytically resistant.

Item 24. The method of any one of items 14-23, wherein the first protein is an antigen binding fragment and the antigen binding fragment comprises a Fab, scFv, or scFab.

Item 25. The method of item 24, wherein the antigen binding fragment is a Fab.

Item 26. The method of any one of items 14-25, wherein the periplasmic fusion protein further comprises a purification tag attached to an N-terminus or a C-terminus of the binding motif.

Item 27. The method of any one of items 14-25, wherein binding motif links the C-terminus of the first protein to the N-terminus of a second protein or the N-terminus of the first protein to the C-terminus of a second protein.

Item 28. The method of item 14, wherein the *E. coli* host cells are a mutant *E. coli* TG1 F- strain having DSM accession number 33004, deposited on Jan. 8, 2019.

Item 29. The method of item 15 or 16, wherein the *E. coli* host cells are a mutant *E. coli* TG1 F- strain having DSM accession number 33005, deposited on Jan. 8, 2019.

Item 30. An *E. coli* TG1, TG1 F-, XL1 Blue, MC1061, SS320, BL21, JM83, JM109, HB2151, W3110, or Cmax5 alpha strain having reduced or no Tsp protein activity as compared to a wild-type cell resulting from a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity.

Item 31. The *E. coli* strain of item 30 comprising a nucleic acid encoding a periplasmic fusion protein comprising a binding motif and the binding motif comprises SEQ ID NO: 1 or a sequence with at least 60% sequence identity to SEQ ID NO: 1.

Item 32. An *E. coli* TG1, TG1 F-, XL1 Blue, MC1061, SS320, BL21, JM83, JM109, HB2151, W3110, or Cmax5 alpha strain having reduced or no Tsp protein activity and ompT protein activity as compared to a wild-type cell resulting from:
  a) a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity; and
b) a mutation in the ompT gene that encodes a mutated ompT protein and the mutation reduces or eliminates protease activity, or a mutation in the ompT gene or regulatory sequence of the ompT gene that reduces or eliminates expression of the ompT protein, or one or more deletions of regions in the bacterial chromosome that reduces or eliminates ompT protein activity.

Item 33. The *E. coli* strain of item 32 comprising:
a nucleic acid encoding a periplasmic fusion protein comprising a binding motif and the binding motif comprises SEQ ID NO: 2 or a sequence with at least 70% sequence identity to SEQ ID NO: 2 or a nucleic acid encoding a periplasmic fusion protein comprising a binding motif and the binding motif comprises SEQ ID NO: 36 or a sequence with at least 78% sequence identity to SEQ ID NO: 36.

Item 34. The *E. coli* strain of any one of items 30-33, wherein the binding motif is proteolytically sensitive.

Item 35. The *E. coli* strain of any one of items 30-33, wherein the binding motif is proteolytically resistant.

Item 36. A mutant *E. coli* strain:

a) having reduced or no Tsp protein activity as compared to a wild-type cell resulting from a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity;

for the expression of periplasmic fusion protein comprising a binding motif attached to a first protein or embedded within an amino acid sequence of the first protein; the binding motif comprises SEQ ID NO: 1 or a sequence with at least 60% sequence identity to SEQ ID NO: 1; or b) having reduced or no Tsp protein activity and ompT protein activity as compared to a wild-type cell resulting from:

i) a mutation in the Tsp gene that encodes a mutated Tsp protein and that reduces or eliminates protease activity, or a mutation in the Tsp gene or regulatory sequence of the Tsp gene that reduces or eliminates expression of the Tsp protein, or one or more deletions of regions in the bacterial chromosome that reduce or eliminate Tsp protein activity; and ii) a mutation in the ompT gene that encodes a mutated ompT protein and that reduces or eliminates protease activity, or a mutation in the ompT gene or regulatory sequence of the ompT gene that reduces or eliminates expression of the ompT protein, or one or more deletions of regions in the bacterial chromosome that reduces or eliminates ompT protein activity;

for the expression of periplasmic fusion protein comprising a binding motif attached to a first protein or embedded within an amino acid sequence of the first protein; the binding motif comprises SEQ ID NO: 2 or SEQ ID NO: 36 or a sequence with at least 70% sequence identity to SEQ ID NO:2 or at least 78% sequence identity to SEQ ID NO: 36, respectively.

Item 37. A mutant *E. coli* TG1 F- strain having DSM accession number 33004 or 33005, both deposited on Jan. 8, 2019.

EXAMPLES

The following examples are provided by way of illustration only and not by way of limitation. Those of skill in the art will readily recognize a variety of non-critical parameters that could be changed or modified to yield essentially the same or similar results.

Figure 2:
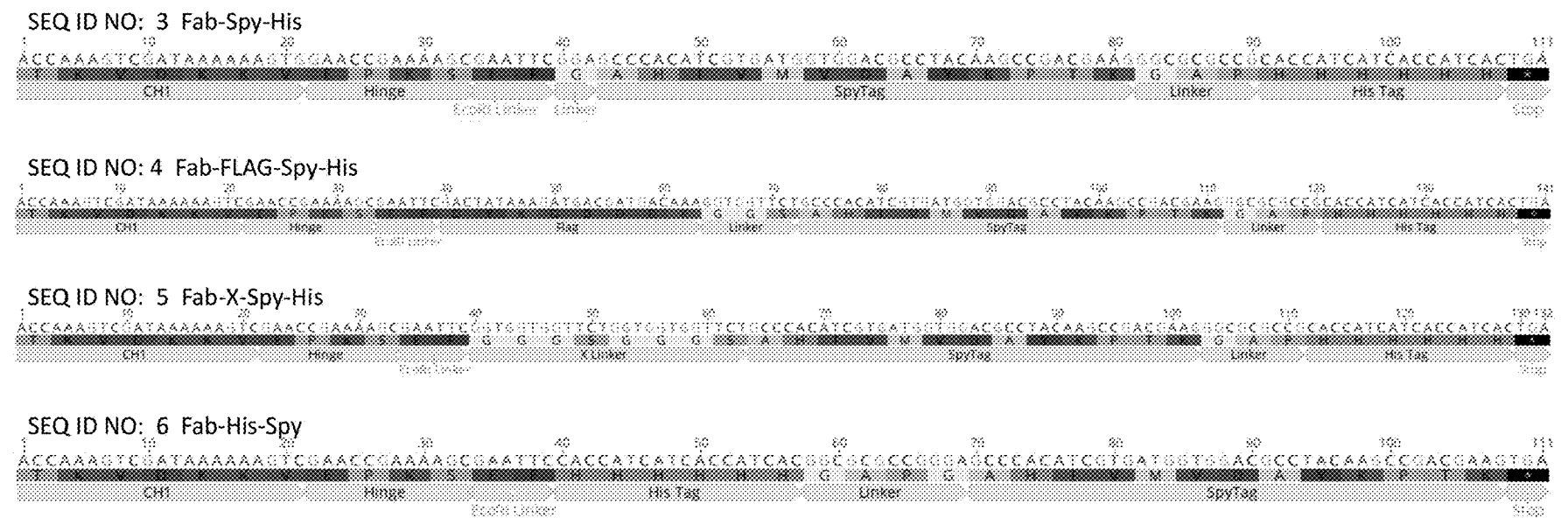

Example 1—Periplasmic Expression of Fab-X-SpyTag Fusion Proteins in which X is a Linker Genes encoding human antibody fragments in the Fab format with a SpyTag at the C-terminus of the truncated heavy chain (i.e., Fab-SpyTag constructs) were cloned into an expression vector having signal sequences at the H and L chains of the Fab, which direct the nascent chains into the periplasm by a bacterial transport. The Fab genes used in this example encoded non-covalent heterodimers of the light chain (without the C-terminal cysteine) with a truncated heavy chain having the VH domain, CH1 domain, and the first 4 amino acids of the hinge region (up to, but not including the first hinge cysteine). *E. coli* TG1 F- (without F-episome; Bio-Rad) was then transformed with such vectors. Fab constructs derived from five different antibodies were tested. Partial sequences for the constructs are shown in FIG. 2. The transformants were cultured in 250 mL 2×YT broth with 0.1% glucose and chloramphenicol. The cultures were induced with 0.8 mM IPTG after 1 hour of growth at 37°. Expression was allowed to proceed for approximately 16 hours at 30°. The cultures were centrifuged and the cells were frozen at −80°. The cells were lysed with BugBuster lysis buffer (Millipore-Sigma). The fusion proteins were then purified via affinity chromatography (e.g., by Ni-NTA chromatography for fusion proteins having a hexahistidine tag or by Strep-Tactin® chromatography for fusion proteins having a Strep-tag®) and buffer exchanged into 3×PBS. Purity of the fusion protein was determined by SDS-PAGE using non-reducing conditions, 4-20% polyacrylamide gels (Bio-Rad Mini-PROTEAN TGX), and Coomassie® stain. Further, all purified Fab fragments were tested for functionality by ELISA (at 2 µg/ml) using the Fab antigen (5 µg/ml in PBS coated on the surface of microtiter plate wells overnight at 4° C.). Binding of the Fab fragment to its antigen was detected with an HRP conjugated anti-Fab (STAR126P, Bio-Rad) or anti-histidine tag (MCA1396P, Bio-Rad) secondary antibody and QuantaBlu fluorescence substrate (Thermo Fisher).

Initial attempts to purify Fab-SpyTag fusion proteins were not successful. Constructs containing a FLAG-SpyTag-His peptide sequence at the C-terminus of the Fab heavy chain (SEQ ID NO: 4) could not be purified, which was similar to all other constructs that had the purification tag (His tag or Strep-Tag®) on the C terminal end of the SpyTag (SEQ ID NO: 3-5 and 8-10). On the other hand, constructs containing a His-SpyTag or His-SpyTag-FLAG peptide sequence at the C-terminus of the Fab heavy chain (SEQ ID NO: 6 and 7, respectively) could be purified, but those constructs where not reactive in a subsequent SpyTag-SpyCatcher protein ligation reaction. To test for protein ligation of the SpyTag portion of the fusion proteins with SpyCatcher, each fusion protein (final concentration 15 µM) was mixed with SpyCatcher (final concentration 20 µM) in 1×PBS buffer and allowed to couple for 2 hours at room temperature. SpyCatcher was produced by bacterial cytoplasmic expression and purified via Ni NTA as described by Zakeri et al. (2012). SDS-PAGE was used to test for the appearance of a new band on the gel which corresponds to the SpyTag fusion-SpyCatcher coupling product. A new SpyTag fusion protein-SpyCatcher band of correct size was not observed for any of the fusion proteins, indicating that none of the fusion proteins coupled to SpyCatcher and that the SpyTag portion of the fusion protein was not intact nor fully functional. Without being bound by theory, applicants hypothesized that the SpyTag was susceptible to cleavage by one or more periplasmic proteases.

Figures 3, 4:
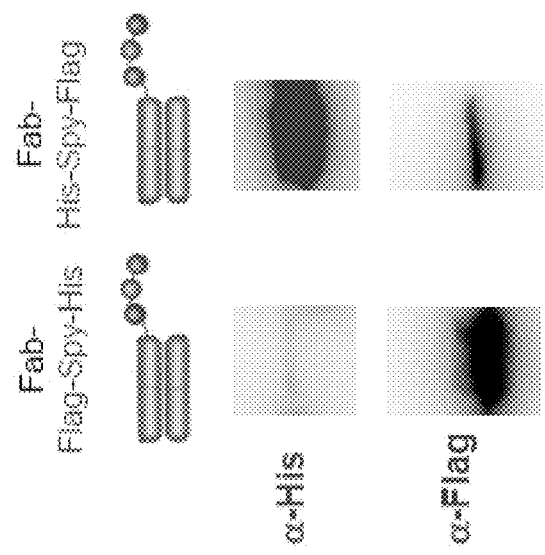
FIG. 3 shows Western blot results from periplasmic expression studies as described in Example 1.
FIG. 4 illustrates the partial nucleotide and amino acid sequences of MBP-SpyTag constructs used in periplasmic expression studies as described in Example 2.

To determine where cleavage occurred in the fusion proteins, the expression products of Fab-FLAG-SpyTag-His (SEQ ID NO: 4) and Fab-His-SpyTag-FLAG (SEQ ID NO: 7) fusion proteins were analyzed by Western blot analysis (SDS PAGE with reducing sample buffer (Bio-Rad), AnyKD TGX gels (Bio-Rad), transfer onto PVDF membranes (Bio-Rad)). The expression products of the fusion proteins were analyzed prior to purification by Western blot analysis using HRP-labeled anti-FLAG® antibody (Sigma A8592) or HRP-labeled anti-Histidine-Tag-Antibody (Bio-Rad MCA1396P) for detection. The Western blot results are shown in FIG. 3.

Results: As illustrated in the Western blots in FIG. 3, the expression product of the Fab-FLAG-SpyTag-His fusion protein was recognized by a labeled anti-FLAG® antibody but not an anti-histidine-tag antibody, indicating that a histidine-tag-containing portion was cleaved from the C-terminus of the fusion protein, i.e., cleavage occurred after the FLAG sequence. The expression product of the Fab-His-SpyTag-FLAG fusion protein was recognized by labeled anti-histidine-tag antibody but not by labeled anti-FLAG antibody, indicating that a FLAG-containing portion of the fusion protein was cleaved from the C-terminus of the fusion protein, i.e., cleavage occurred after the histidine-tag.

MALDI-TOF-Mass spectrometry (4800 MALDI TOF/TOF Analyzer, AB Sciex) was used to determine the mass of light chain and heavy chain peptide of the expression products of Fab-His-SpyTag (SEQ ID NO: 6) purified via Ni-NTA. The sample was desalted (ZipTip C4, Merck Millipore) and co-crystallized with sinapic acid. Mass was determined in linear mode between 5000-50000 m/z. 4000 laser shots were added for one spectrum. Protein standard I (Bruker) was used for mass calibration. Mass spectrometry results are below.

Light Chain:

| Mass calc. (full length) | 22691 Da |
| Mass found (m/z) | 22691 Da |

Heavy Chain

| Mass calc. (full length) | 26437 Da |
| Mass found (m/z) | 25416 Da |
| Mass calc. (−9aa) | 25403 Da |

The mass spectrometry results showed that 9 amino acids were cleaved off the C-terminal end of the Fab-His-SpyTag fusion protein. Thus, 9 amino acid residues from the C-terminal end of SpyTag (which is 13 amino acids in length: AHIVMVDAYKPTK; SEQ ID NO: 1) were cleaved after valine at amino acid position 4 by a protease in the E. coli periplasm. Without wishing to be bound by theory, applicants believe that, since the SpyTag was cleaved in all constructs, cleavage of SpyTag is independent of the amino acid sequence before and after the SpyTag.

Example 2—Periplasmic Expression of Various Maltose Binding Protein-SpyTag Fusion Proteins Genes encoding Maltose Binding Protein (MBP) either with FLAG-SpyTag-His tag (SEQ ID NO: 11) or His-SpyTag-FLAG tag (SEQ ID NO: 12) at the C terminus were cloned into an expression vector for periplasmic expression and transformed into E. coli TG1F-. The MBP used in this example had 4 amino acids removed from the C-terminus. Partial sequences for the MBP-containing constructs are shown in FIG. 4. Expression and purification of the constructs was performed as described in Example 1.

Initial attempts at purifying periplasmic expressed MBP-SpyTag fusion proteins were not successful. Similar to the Fab fragments in Example 1, periplasmic constructs containing a FLAG-SpyTag-His peptide sequence at the C-terminus of MBP could not be purified. Constructs containing a His-SpyTag-FLAG peptide sequence at the C-terminus of MBP could be purified but were not reactive in a subsequent SpyTag-SpyCatcher protein ligation reaction. Western blot analysis of the expression products before purification as described in Example 1 gave similar results in that the first tag of each construct could be detected but the last tag could not be detected.

MALDI-TOF-Mass spectrometry analysis of the MBPΔ4aa-His-SpyTag-FLAG construct (SEQ ID NO: 12) was performed as described in Example 1. Mass spectrometry results are below.

Full-Length Protein:

| Mass calc. (full length) | 44241 Da |
| Mass found (m/z) | 44273 Da (full-length) |
| Mass found (m/z) | 42032 Da (main product) |
| Mass calc. (1-382aa) | 42011 Da |

The mass spectrometry results showed small amounts of full-length protein. However, the main product consisted of amino acids 1-382, indicating that cleavage occurred after the valine at amino acid position 4 of SpyTag. This is the same position at which cleavage occurred for the Fab fragments in Example 1. Without wishing to be bound by theory, applicants believe that cleavage of the SpyTag was not dependent upon the Fab amino acid sequence or structure as cleavage also occurred with a structurally completely independent protein (i.e., MBP). Mass spectrometry analysis also showed that the ompT signal peptide for transport to the periplasm was cleaved off, which occurs after transfer of the protein to the periplasm. Since expression of full-length SpyTag fusion proteins in the cytoplasm has been described in Keeble et al. (2019), applicants hypothesized that the SpyTag cleavage described in Examples 1 and 2 occurred in the periplasm.

To test this hypothesis, MBP with a FLAG-SpyTag and His tag at the C terminus was cloned without the ompT signal peptide into an expression vector for cytoplasmic expression and transformed into E. coli. Expression and purification was performed as described in Example 1. Cytoplasmic expression of the construct resulted in high yields (about 11 mg/L) of full-length product.

Periplasmic expression of Fab and MBP-SpyTag fusion proteins led to truncated proteins with a cleaved SpyTag and cytoplasmic expression of MBP with an identical amino acid sequence (without the signal peptide) gave full-length product. Without being bound by theory, applicants hypothesized that cleavage of the SpyTag was caused by one or more periplasmic proteases.

Example 3—Periplasmic Expression of a scFv-SpyTag Fusion Protein

Genes encoding scFv with FLAG-SpyTag-His (SEQ ID NO: 34; FIG. 9) at the C terminus were cloned into an expression vector for periplasmic expression and transformed into E. coli TG1F-. Partial sequences for the scFv constructs are shown in FIG. 9. Expression and purification of the construct was performed as described in Example 1.

Initial attempts to purify periplasmically expressed scFv-SpyTag fusion proteins were not successful. Similar to the Fab fragments in Example 1 and the MBP constructs in Example 2, periplasmic scFv constructs containing a FLAG-SpyTag-His peptide sequence at the C-terminus of the scFv could not be purified via the His tag.

Example 4—Periplasmic Expression of FabX-SpyTag Fusion Proteins in which X is a Linker in Various Bacterial Strains The Fab-SpyTag-His (SEQ ID NO: 3) and Fab-FLAG-Spy-His (SEQ ID NO: 4) constructs were each transformed into the following *E. coli* strains for periplasmic expression to determine which periplasmic protease (s) was/were cleaving SpyTag:
1. TG1 F- (without F-episome; Bio-Rad)
2. Jw0157: degP- (Yale *Coli* Genetic Stock Center)
3. KS476: degP- (Yale *Coli* Genetic Stock Center)
4. KS1000: prc- (or tsp-) (New England Biolabs)
5. JW3203: degQ- (Yale *Coli* Genetic Stock Center)
6. 27C2: degP-, ptr3-, ompT- (ATCC)
7. HM130: degP-, ptr-, ompT-, tsp-, eda (U. of Texas at Austin)

The transformants were cultured, expressed and purified as described in Example 1. The concentration of the purified fusion proteins with each *E. coli* strain was determined and the expression products of each fusion were analyzed by SDS-PAGE with non-reducing conditions. Expression of full-length Fab (including the tags) was visible as a heavy chain and light chain on SDS-PAGE, while SpyTag-cleavage resulted in Fabs without purification tags, which were not purified. Both types of fusion proteins were expressed as full length protein in only the KS1000 (tsp-) and HM130 (degP-, ptr-, ompT-, tsp-, eda) strains, indicating that tsp protease is involved in cleaving SpyTag.

Example 5—Generation of Knock Out Cell Strains Using TG1 F-Strain for Fab-SpyTag Constructs Because all the expression strains used in Example 4 except for TG1 F- did not grow well and/or did not give high yields of properly folded, soluble Fab, TG1 F- protease knock out strains were constructed to increase the yield of Fab fused to SpyTag.

Mutant *E. coli* TG1 F- cell strains were generated in which the tsp gene, the degP gene or both tsp and depP genes were knocked out as described by Datsenko and Wanner (2000), *Proc Natl Acad Sci USA*, 97 (12): 6640-6645. Briefly, the genes were knocked out by transforming a PCR product with homologous flanking regions containing FRT sites and an antibiotic resistance gene together with a plasmid containing λ recombinase. Clones were selected by antibiotic resistance in which the gene was replaced with the PCR product through recombination. In the next step, these clones were transfected with Flp recombinase, leading to the excision of the resistance gene.

Fab-SpyTag-His and Fab-FLAG-Spy-His constructs (i.e., the same constructs as in Example 4) were transformed into the strains constructed above, i.e., TG1F-Δtsp (SK4, DSMZ accession number DSM 33004), TG1 F-ΔdegP, and TG1 F-Δtsp ΔdegP double knock out. Expressed fusion proteins were purified and analyzed by SDS-PAGE as described in Example 1.

Results: Both types of fusion proteins were expressed as full length protein in TG1 F-Δtsp strain (SK4) and in TG1 F-Δtsp ΔdegP double knock out strain but not in TG1 F-ΔdegP strain, indicating that degP is not involved in SpyTag cleavage. Furthermore, expressions in TG1 F-Δtsp and TG1 F-Δtsp ΔdegP gave comparable yields leading to the conclusion that only tsp cleaves SpyTag.

Figure 5:
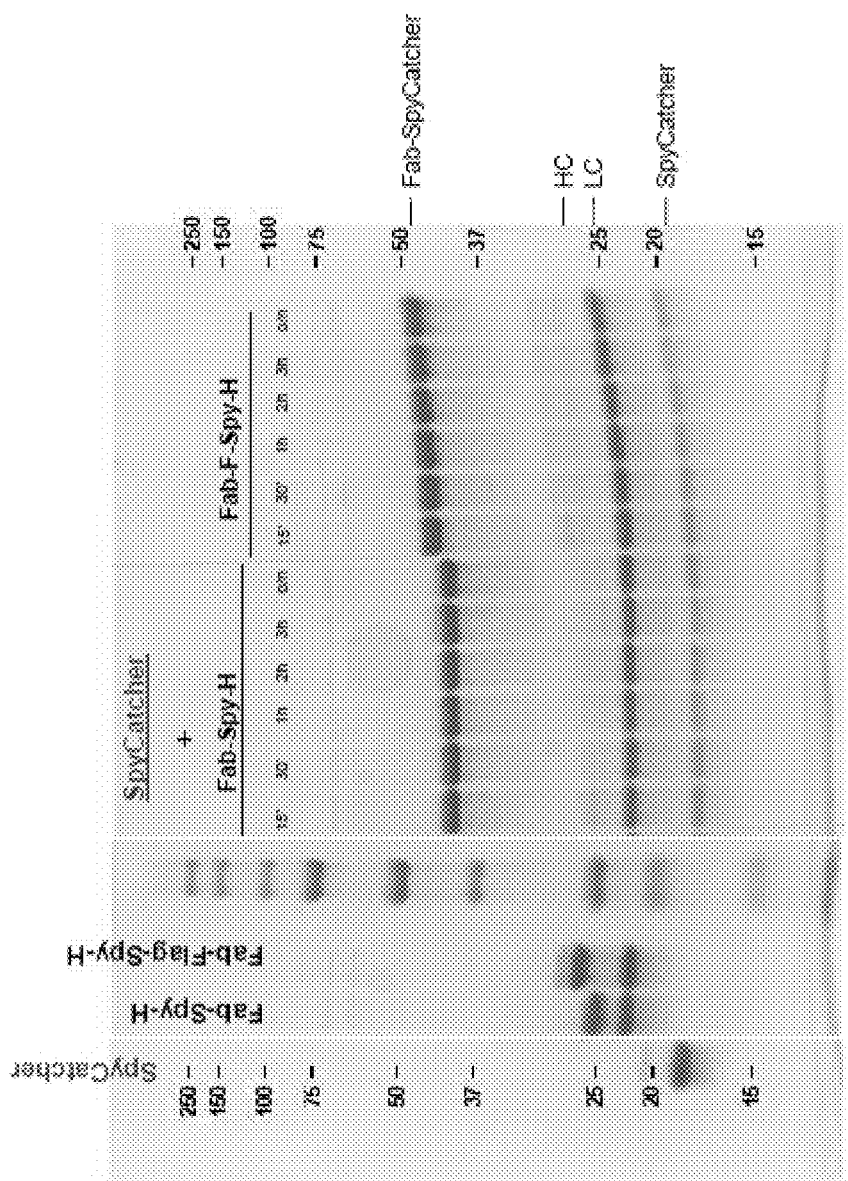
FIG. 5 is an image of an SDS-PAGE gel showing Fab-SpyTag-His and Fab-FLAG-SpyTag-His fusion proteins reacting with SpyCatcher over time (see Example 5). As the SpyTag coupled with SpyCatcher, the heavy chain (HC) band disappeared and a new band corresponding to the SpyTag fusion-SpyCatcher coupling product appeared.

Fab-SpyTag-His and Fab-FLAG-SpyTag-His constructs were next tested for their ability to form a covalent bond with SpyCatcher by protein ligation. SpyCatcher was produced by bacterial cytoplasmic expression and purified via Ni NTA as described by Zakeri et al. (2012). The fusion proteins were expressed and purified using SK4 strain as described above. Each fusion protein (final concentration 15 μM) was mixed with SpyCatcher (final concentration 20 μM) in 1×PBS buffer and allowed to couple for 15 minutes, 30 minutes, 1 hours, 2 hours, 3 hours, and overnight at room temperature. SDS-PAGE was used to test for the appearance of a new band on the gel which corresponds to the SpyTag fusion-SpyCatcher coupling product (see FIG. 5). A new SpyTag fusion-SpyCatcher band of correct size was observed for both fusion proteins, indicating that Fab-SpyTag-H and Fab-FLAG-SpyTag-H both coupled to SpyCatcher, and that the SpyTag portion of the fusion protein was intact and fully functional.

Example 6—Periplasmic Expression of a MBP-SpyTag Fusion Protein in Protease Knock Out Strains The gene encoding Maltose Binding Protein (MBP) with FLAG-SpyTag-His tag (SEQ ID NO: 11, FIG. 4) at the C terminus was cloned into an expression vector for periplasmic expression and transformed into *E. coli* SK4 strain. The most commonly found MBP sequence in fusion proteins for protein crystallization studies is truncated by 4 amino acids at the C terminus (Waugh, 2016). This sequences was used for these experiments. Expression and purification of the construct was performed as described in Example 1. Full-length protein with high yield (about 10 mg/L) was produced by using the tsp protease knock out strain.

Example 7—Periplasmic Expression of scFv-SpyTag Fusion Proteins in Protease Deficient Bacterial Strains The gene encoding scFv with FLAG-SpyTag-His (SEQ ID NO: 34; FIG. 9) at the C terminus was cloned into an expression vector for periplasmic expression and transformed into TG1 F-Δtsp knock out strain. Expression and purification of the construct was performed as described in Example 1. Full-length protein with high yield (about 7 mg/L) was produced by using the tsp protease knock out strain.

Example 8—Generation of Knock Out Cell Strains Using TG1 F-Strain for Fab-SpyTag002 Constructs Genes encoding human antibody fragments in the Fab format with a SpyTag002 at the C-terminus of the truncated heavy chain (i.e., Fab-SpyTag002 constructs, FIG. 6) were cloned into an expression vector having signal sequences at the H and L chains of the Fab, which direct the nascent chains into the periplasm by a bacterial transport. *E. coli* TG1 F- (without F-episome; Bio-Rad) was then transformed with such vectors. Expression and purification of the construct was performed as described in Example 1. All attempts to purify Fab-SpyTag002 fusion proteins with a C terminal His tag (SEQ ID NO: 13 and 14) were not successful. Constructs with a His tag between Fab and SpyTag (SEQ ID NO: 15) could be purified but did not carry a functional SpyTag002.

Expression of a Fab-SpyTag002-His (SEQ ID NO: 13 shown in FIG. 6) constructs (with Fab derived from various antibodies) were tested in the following knock out strains of cells in which expression was successful with constructs having SpyTag instead of SpyTag002:

1. KS1000 (Δtsp)
2. SK4 (TG1 F-Δtsp)
3. TG1 F-Δtsp ΔdegP
4. HM130 strain (Δtsp, ΔdegP, ΔompT, Δptr).

After purification via His-tag, the product was analyzed by SDS-PAGE as in Example 4. Expression of full-length fusion protein failed in KS1000 (Δtsp), SK4 (TG1 F-Δtsp), and TG1 F-Δtsp ΔdegP and was successful in HM130 strain (Δtsp, ΔdegP, ΔompT, Δptr) with an acceptable or "high" yield of purified antibody (i.e., about 10 mg/L).

Figure 6:
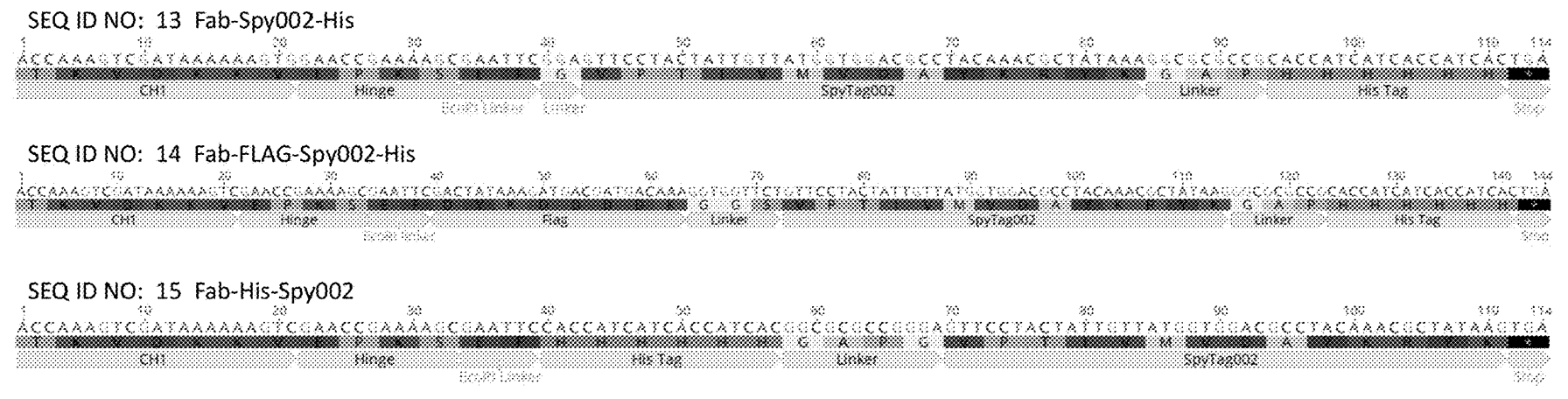

Next, Fab-His-SpyTag002 (SEQ ID NO: 15; FIG. 6) expressed and purified in non-protease deficient TG1 F- strain (i.e., the strain has both tsp and ompT proteases), and in TG1 F-Δtsp ΔdegP strain (i.e., the strain has ompT protease) as described above was analyzed by MALDI-TOF mass spectrometry as described in Example 1 to determine where the fusion protein was cleaved. The mass spectrometry results are below.

TG1 F- Expression of Fab-his-SpyTag002:
Light Chain

| Mass calc. (full length) | 22691 Da |
|---|---|
| Mass found (m/z) | 22682 Da |

Heavy Chain

| Mass calc. (full length) | 26643 Da |
|---|---|
| Mass found (m/z) | 25478 Da |
| Mass calc. (−9aa) | 25488 Da |

TG1 F-ΔTsp ΔdegP Expression of Fab-his-SpyTag002:
Light Chain

| Mass calc. (full length) | 22691 Da |
|---|---|
| Mass found (m/z) | 22680 Da |

Heavy Chain

| Mass calc. (full length) | 26643 Da |
|---|---|
| Mass found (m/z) | 26626 Da (full-length) |
| Mass found (m/z) | 26182 Da (−3 aa) |
| Mass calc. (−3aa) | 26195 Da |

Results: Based on the mass spectrometry results with the non-protease deficient bacterial strain, a 9 amino acid portion was cleaved off of the C-terminus of the fusion protein. This was the same cleavage site observed for SpyTag, which was shown to be cleaved by tsp protease. Based on the mass spectrometry results with the bacterial strain deficient in tsp and degP protease (and having ompT protease), a 3 amino acid portion is cleaved off the C-terminus. Based on all the mass spectrometry results, SpyTag002 (which is 14 amino acids in length: VPTIVMVDAYKRYK; SEQ ID NO: 2) was cleaved by tsp protease after valine at amino acid position 5 and by a second protease after lysine at amino acid position 11. Thus, two different proteases are involved in SpyTag002 cleavage of which one is tsp and the second one, based on the expression results in the 4 strains, can be assumed to be ompT or ptr.

The following TG1 F- knockout strains were made by the same process as described in Example 4: TG1F- ΔompT strain and TG1 F-Δtsp ΔompT strain (SK13, DSMZ accession number DSM 33005). Expression of the Fab-SpyTag002-His constructs (FIG. 6; SEQ ID NO: 13) and Fab-FLAG-SpyTag002-His constructs (FIG. 6; SEQ ID NO:14) was then tested in TG1F- ΔompT strain and TG1 F-Δtsp ΔompT strain as described above. Expression in TG1 F-ΔompT strain did not yield significant amounts of full-length protein because the tsp cleavage site from SpyTag is still present in SpyTag002. Expression of the constructs in a TG1 F-Δtsp ΔompT strain (SK13) was successful and led to full-length proteins with a high protein yield after purification (i.e., about 10 mg/L). Thus, both tsp and ompT proteases are involved in cleaving SpyTag002.

Example 9—Testing of Various Strategies to Protect SpyTag During Periplasmic Expression of Fab-SpyTag Fusion Proteins in a Non-Protease Deficient Bacterial Strain Experiments were performed to determine if SpyTag can be protected from cleavage during expression of SpyTag fusion proteins in non-protease deficient *E. coli* TG1 F- cell strain.

The following strategies were tested to prevent SpyTag cleavage:
1. ST2—A linker with two cysteine residues (CXC) was introduced between FLAG® tag and SpyTag to generate a disulfide bridged loop (Wu et al., 2012). Without being bound by theory, applicants theorized that such a non-linear linker may prevent protease binding: Fab Heavy Chain-Flag-CXC-SpyTag-His6.
2. ST3—A poly-proline linker was introduced into the fusion protein. The poly-proline linker forms a poly-proline helix (Qi et al., 2018). Without being bound by theory, applicants theorized that the poly-proline helix may prevent proteases from binding. Two versions of a fusion protein with a poly-proline linker were made:
    a. Strong: PPPPPPT
    b. Weak: PLPPPF
3. ST4—Two amino acids protrude out of the globular folded domain of the Fab heavy chain (PDB structure accession number 2JB5). These two amino acids were removed and SpyTag was attached to the truncated Fab heavy chain (ending with a conserved valine (IMGT position number 121) and two hinge amino acids, glutamate and proline) without an unfolded linker sequence (see "b" below). Without being bound by theory, applicants theorized that moving the SpyTag closer to the folded domain may prevent the protease from binding.
    a. Fab heavy chain: . . . VEPKS-COOH
    b. ST4: . . . VEP-SpyTag-His
4. ST5—This idea is similar to ST2 but includes FLAG and SpyTag in the disulfide bridged loop: Fab heavy chain-C-Flag-Spy-C-His6.

Figure 7:
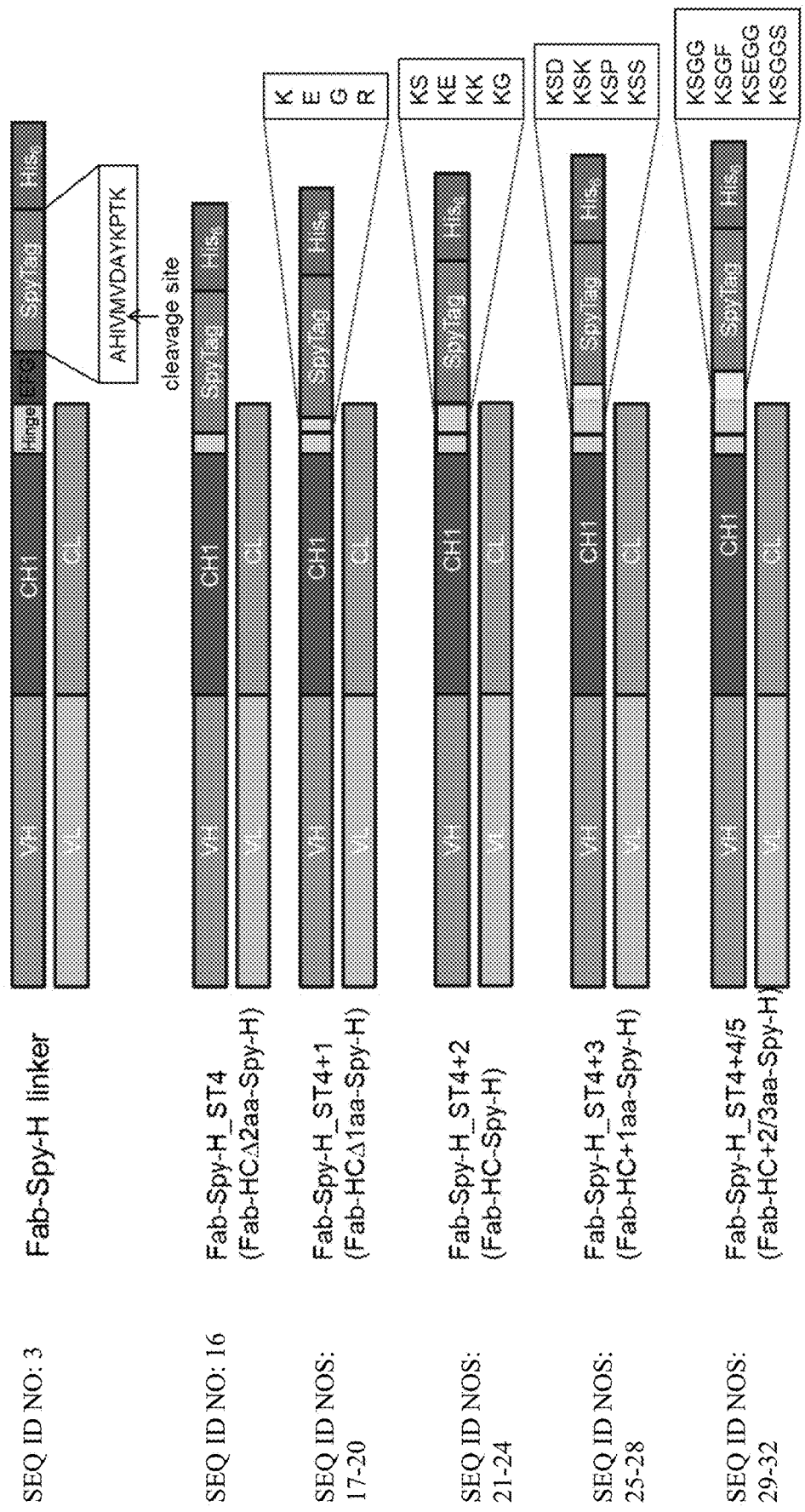
FIG. 7 illustrates the SpyTag-containing constructs used to test various strategies to protect SpyTag during periplasmic expression in a non-protease deficient bacterial strain as described in Example 9.

The above constructs were expressed in a non-protease deficient *E. coli* TG1 F- cell strain, purified via His-tag, and were analyzed by SDS-PAGE as described previously. Only ST4 (SEQ ID NO: 16; FIG. 7) was expressed without SpyTag cleavage. Coupling of ST4 to SpyCatcher was tested as described in Example 5. SDS-PAGE analysis showed no new band for the SpyTag fusion-SpyCatcher coupling product within about 2 hours. Thus, a fusion protein in which two amino acids were removed from the heavy chain of the Fab was expressed without SpyTag cleavage but did not couple to SpyCatcher. Without wishing to be bound by theory, applicant believes that the close proximity of the SpyTag to the folded antibody structure prevented the protease from binding and cleaving the SpyTag but also sterically hindered the SpyCatcher from binding to the SpyTag, which is required for the SpyTag-SpyCatcher reaction.

Further constructs based on the ST4 design, which are summarized in FIG. 7 (SEQ ID NO: 17-32), were made and tested as described previously to determine if SpyTag was cleaved. The constructs were also tested for the ability of SpyTag to couple to SpyCatcher as described in Example 5. The full-length expression yields and ligation results of all the ST4 constructs are summarized in Table 1. A "high" indicates that the fusion protein expression yield was between about 5-10 mg/L, a "low" indicates that the expression yield was about 2-4 mg/L, and a "very low" indicates that the expression yield was less than about 2 mg/L.

TABLE 1

| Fusion Protein | Expression Yield (mg/L) | Ligates to SpyCatcher? |
| --- | --- | --- |
| ST4 (Fab heavy chain Δ2aa-Spy-H) (SEQ ID NO: 16) | High | No |
| ST4 + 1 (Fab heavy chain Δ1aa-Spy-H) (SEQ ID NOS: 17-20) | High | No |
| ST4 + 2 (Fab heavy chain-Spy-H) (SEQ ID NOS: 21-24) | High | Yes |
| ST4 + 3 (Fab heavy chain + 1aa-Spy-H; linker of 1 amino acid between SpyTag and heavy chain of Fab) (SEQ ID NOS: 25-28) | Low | Yes |
| ST4 + 4/5 (Fab heavy chain + 2/3 aa-Spy-H; linker of 2 or 3 amino acids between SpyTag and heavy chain of Fab) (SEQ ID NOS: 29-32) | very low | Yes |

The results in Table 1 show that SpyTag attached directly to the C-terminus of the Fab heavy chain (or ST4+2) gave the best overall performance in that the fusion protein exhibited a high yield of full-length protein (i.e., about 5-10 mg/L) and ligated to SpyCatcher. Fusion proteins having a 1, 2, or 3 amino acid linker between the C-terminus of the Fab heavy chain and SpyTag (i.e., ST4+3 and ST4+4/5) were cleaved significantly by proteases, resulting in low or very low yields of full-length protein. Without being bound by theory, applicants believe that the longer the linker between the C-terminus of the folded Fab globular domain and SpyTag, the more the SpyTag is accessible to cleavage and for ligation to SpyCatcher. Applicants also believe that a fusion protein having SpyTag attached directly to the C-terminus of the Fab heavy chain is the optimal compromise between attaching the SpyTag close to the folded domain of Fab to avoid periplasmic protease cleavage and allowing sufficient space to sterically enable ligation of SpyTag to SpyCatcher.

Example 10—Testing of Strategies to Protect SpyTag During Periplasmic Expression of Maltose-Binding Protein-SpyTag Fusion Proteins in a Non-Protease Deficient Bacterial Strain Experiments were performed to test the hypothesis that moving SpyTag closer to a folded domain in maltose-binding protein (MBP) protects the SpyTag from periplasmic protease digestion. MBP was chosen because it is a different class of protein than Fab. The MBP sequence used most frequently for crystallization studies is truncated by 4 amino acids at the C terminus (Waugh, 2016). Since crystallization experiments and structure determinations often benefit from an increased rigidity of the protein (i.e., folded domains without flexible linkers) and the same is expected for the stabilization of the SpyTag from protease cleavage, the same sequence was used in this example. Genes encoding MBP with SpyTag-His tag (SEQ ID NO: 33, FIG. 8) directly fused to the C terminus was cloned into an expression vector for periplasmic expression and transformed into E. coli TG1 F- strain. Expression and purification of the construct was performed as described in Example 1. Full-length protein with high yield (about 7 mg/L) was produced in non-protease deficient TG1 F- strain. The construct was tested for the ability of SpyTag to ligate to SpyCatcher as described in Example 5 which was found to be the case.

Attaching the SpyTag directly to the folded domain of MBP led to a fusion protein in which the SpyTag was protected from periplasmic protease cleavage and the SpyTag was still functional, similar to the Fab fusion protein in Example 9 in which the SpyTag was attached directly to the heavy chain. In contrast, the MBP-Flag-SpyTag-His and MBP-His-SpyTag-Flag fusion proteins in Example 2 contain a tag which acts as a linker with 13 and 12 amino acids, respectively, which makes the SpyTag vulnerable to protease cleavage. Without wishing to be bound by theory, applicant believes that these results show that cleavage of SpyTag fused without a linker to the C-terminus of Fab (i.e., the Fab-SpyTag fusion proteins tested in Example 9) was not dependent on the Fab structure because cleavage also occurred when SpyTag was fused via a linker to the C-terminus of MBP, which is structurally unrelated to Fab.

Example 11—Testing of Strategies to Protect SpyTag During Periplasmic Expression of scFv-SpyTag Fusion Proteins in a Non-Protease Deficient Bacterial Strain Experiments were performed to test the hypothesis that moving SpyTag closer to a folded domain in scFv protects the SpyTag from periplasmic protease digestion. ScFv was chosen because it is a different protein and has a different structure than Fab or MBP. The scFv used in this example had 6 amino acids removed from the C-terminus, resulting in a scFv truncated within its light chain FR4 region (encoded by the J genes). A scFv(Δ6aa)-SpyTag-His fusion construct (SEQ ID NO: 35; FIG. 9) in which SpyTag-His is fused directly (i.e., without a linker sequence) to the C-terminus of a C-terminally truncated scFv was cloned into an expression vector for periplasmic expression and transformed into E. coli TG1F-. Expression and purification of the fusion protein was performed as described in Example 1. Full-length protein was produced with a high yield (about 8 mg/L), indicating that attaching SpyTag directly to scFv protects SpyTag from periplasmic cleavage.

Example 12—Periplasmic Expression of Fab-SpyTag003 Fusion Proteins in Protease Deficient Bacterial Strains Genes encoding human antibody fragments in the Fab format with a SpyTag003 at the C-terminus of the truncated heavy chain i.e., construct of SEQ ID 3 and 4 with SpyTag002 replaced with SpyTag003 (SEQ ID NO: 36) were cloned into an expression vector for periplasmic expression as described in Example 1. Transformation of the plasmid into E. coli TG1 F- or SK4 strain and expression and purification of the construct was performed as described in Example 1. All attempts to purify Fab-SpyTag003 fusion proteins were not successful.

The plasmids were transformed into SK13 strain and expressed and purified as described in Example 1. Expression of the constructs in a TG1 F-Δtsp ΔompT strain (SK13) was successful and led to full-length proteins with a good protein yield after purification (i.e., about 6 mg/L). Thus, both tsp and ompT proteases are involved in cleaving SpyTag003.

All patents, patent applications, and other published reference materials cited in this specification are hereby incorporated herein by reference in their entirety.

SEQ ID NO: 1 (SpyTag)

```
           AHIVMVDAYK PTK
```

SEQ ID NO: 2 (SpyTag002)

```
           VPTIVMVDAY KRYK
```

SEQ ID NO: 3 (Fab-Spy-His; partial amino acid sequence starting with the first 4 amino acid residues of the human IgG1 hinge domain; human Ig CH1 according to IMGT definition, ending with a conserved valine at IMGT position number 121)

```
           Human CH1-
           EPKSEFGAHIVMVDAYKPTKGAPHHHHHH
```

SEQ ID NO: 4 (Fab-FLAG-Spy-His; partial amino acid sequence starting with the first 4 amino acid residues of the human IgG1 hinge domain; human Ig CH1 according to IMGT definition, ending with a conserved valine at IMGT position number 121)

```
           Human CH1-
           EPKSEFDYKDDDDKGGSAHIVMVDAYKPTKGAPHHHHHH
```

SEQ ID NO: 5 (Fab-X-Spy-His; partial amino acid sequence starting with the first 4 amino acid residues of the human IgG1 hinge domain; human Ig CH1 according to IMGT definition, ending with a conserved valine at IMGT position number 121)

```
           Human CH1-
           EPKSEFGGGSGGGSAHIVMVDAYKPTKGAPHHHHHH
```

SEQ ID NO: 6 (Fab-His-Spy; partial amino acid sequence starting with the first 4 amino acid residues of the human IgG1 hinge domain; human Ig CH1 according to IMGT definition, ending with a conserved valine at IMGT position number 121)

```
           Human CH1-
           EPKSEFHHHHHHGAPGAHIVMVDAYKPTK
```

SEQ ID NO: 7 (Fab-His-Spy-FLAG; partial amino acid sequence starting with the first 4 amino acid residues of the human IgG1 hinge domain; human Ig CH1 according to IMGT definition, ending with a conserved valine at IMGT position number 121)

```
           Human CH1-
           EPKSEFHHHHHHGAPGAHIVMVDAYKPTKGGSDYKDDDDK
```

SEQ ID NO: 8 (Fab-Spy-Sx2; partial amino acid sequence starting with the first 4 amino acid residues of the human IgG1 hinge domain; human Ig CH1 according to IMGT definition, ending with a conserved valine at IMGT position number 121)

```
Human CH1-
EPKSEFGAHIVMVDAYKPTKGAPSAWSHPQFEKGGGSGGGSGGSAWSHPQ
FEK
```

SEQ ID NO: 9 (Fab-FLAG-Spy-Sx2; partial amino acid sequence starting with the first 4 amino acid residues of the human IgG1 hinge domain; human Ig CH1 according to IMGT definition, ending with a conserved valine at IMGT position number 121)

```
Human CH1-
EPKSEFDYKDDDDKGGSAHIVMVDAYKPTKGAPSAWSHPQFEKGGGSGGGS
GGSAWSHPQFEK
```

SEQ ID NO: 10 (Fab-X-Spy-Sx2; partial amino acid sequence starting with the first 4 amino acid residues of the human IgG1 hinge domain; human Ig CH1 according to IMGT definition, ending with a conserved valine at IMGT position number 121)

```
Human CH1-
EPKSEFGGGSGGGSAHIVMVDAYKPTKGAPSAWSHPQFEKGGGSGGGSG
GSAWSHPQFEK
```

SEQ ID NO: 11 (MBP(Δ4aa)-FLAG-Spy-His)

```
MKKTAIAIAVALAGFATVAQAKIEEGKLVIWINGDKGYNGLAEVGKKFE
KDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPP
KTWEEIPALDKELKAKGKSALMFNLQEPYFTWPLIAADGGYAFKYENGK
YDIKDVGVDNAGAKAGLTFLVDLIKNKHMNADTDYSIAEAAFNKGETAM
TINGPWAWSNIDTSKVNYGVTVLPTFKGQPSKPFVGVLSAGINAASPNK
ELAKEFLENYLLTDEGLEAVNKDKPLGAVALKSYEEELAKDPRIAATME
NAQKGEIMPNIPQMSAFWYAVRTAVINAASGRQTVDEALKDAQTEFDYK
DDDDKGGSAHIVMVDAYKPTKGAPHHHHHH
```

SEQ ID NO: 12 (MBP(Δ4aa)-His-Spy-FLAG)

```
MKKTAIAIAVALAGFATVAQAKIEEGKLVIWINGDKGYNGLAEVGKKFE
KDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPP
KTWEEIPALDKELKAKGKSALMFNLQEPYFTWPLIAADGGYAFKYENGK
YDIKDVGVDNAGAKAGLTFLVDLIKNKHMNADTDYSIAEAAFNKGETAM
TINGPWAWSNIDTSKVNYGVTVLPTFKGQPSKPFVGVLSAGINAASPNK
ELAKEFLENYLLTDEGLEAVNKDKPLGAVALKSYEEELAKDPRIAATME
NAQKGEIMPNIPQMSAFWYAVRTAVINAASGRQTVDEALKDAQTEFHHH
HHHGAPGAHIVMVDAYKPTKGGSDYKDDDDK
```

SEQ ID NO: 13 (Fab-Spy2-His; partial amino acid sequence starting with the first 4 amino acid residues of the human IgG1 hinge domain; human Ig CH1 according to IMGT definition, ending with a conserved valine at IMGT position number 121)

```
Human CH1-
EPKSEFGVPTIVMVDAYKRYKGAPHHHHHH
```

SEQ ID NO: 14 (Fab-FLAG-Spy2-His; partial amino acid sequence starting with the first 4 amino acid residues of the human IgG1 hinge domain; human Ig CH1 according to IMGT definition, ending with a conserved valine at IMGT position number 121)

```
Human CH1-
EPKSEFDYKDDDDKGGSVPTIVMVDAYKRYKGAPHHHHHH
```

SEQ ID NO: 15 (Fab-His-Spy2; partial amino acid sequence starting with the first 4 amino acid residues of the human IgG1 hinge domain; human Ig CH1 according to IMGT definition, ending with a conserved valine at IMGT position number 121)

```
Human CH1-EPKSEFHHHHHHGAPGVPTIVMVDAYKRYK
```

SEQ ID NO: 16 (Fab-Spy-His_ST4 (HC Δ2aa); partial amino acid sequence starting with the first 2 amino acid residues of the human IgG1 hinge domain; human Ig CH1 according to IMGT definition, ending with a conserved valine at IMGT position number 121):

```
Human CH1-EPAHIVMVDAYKPTKGAPHHHHHH
```

SEQ ID NO: 17 (Fab-Spy-His_ST4+1 (HC Δ1aa); partial amino acid sequence starting with the first 3 amino acid residues of the human IgG1 hinge domain; human Ig CH1 according to IMGT definition, ending with a conserved valine at IMGT position number 121):

```
Human CH1-EPKAHIVMVDAYKPTKGAPHHHHHH
```

SEQ ID NO: 18 (Fab-Spy-His_ST4+1 (HC Δ1aa); partial amino acid sequence starting with the first 2 amino acid residues of the human IgG1 hinge domain and the third amino acid residue replaced with "E"; human Ig CH1 according to IMGT definition, ending with a conserved valine at IMGT position number 121):

```
Human CH1-EPEAHIVMVDAYKPTKGAPHHHHHH
```

SEQ ID NO: 19 (Fab-Spy-His_ST4+1 (HC Δ1aa); partial amino acid sequence starting with the first 2 amino acid residues of the human IgG1 hinge domain and the third amino acid residue replaced with "G"; human Ig CH1 according to IMGT definition, ending with a conserved valine at IMGT position number 121):

```
Human CH1-EPGAHIVMVDAYKPTKGAPHHHHHH
```

SEQ ID NO: 20 (Fab-Spy-His_ST4+1 (HC Δ1aa); partial amino acid sequence starting with the first 2 amino acid residues of the human IgG1 hinge domain and the third amino acid residue replaced with "R"; human Ig CH1 according to IMGT definition, ending with a conserved valine at IMGT position number 121):

```
Human CH1-EPRAHIVMVDAYKPTKGAPHHHHHH
```

SEQ ID NO: 21 (Fab-Spy-His_ST4+2 (HC); partial amino acid sequence starting with the first 4 amino acid residues of the human IgG1 hinge domain; human Ig CH1 according to IMGT definition, ending with a conserved valine at IMGT position number 121):

```
Human CH1-EPKSAHIVMVDAYKPTKGAPHHHHHH
```

SEQ ID NO: 22 (Fab-Spy-His_ST4+2 (HC); partial amino acid sequence starting with the first 3 amino acid residues of the human IgG1 hinge domain and the fourth amino acid residue replaced with "E"; human Ig CH1 according to IMGT definition, ending with a conserved valine at IMGT position number 121):

```
Human CH1-EPKEAHIVMVDAYKPTKGAPHHHHHH
```

SEQ ID NO: 23 (Fab-Spy-His_ST4+2 (HC); partial amino acid sequence starting with the first 3 amino acid residues of the human IgG1 hinge domain and the fourth amino acid residue replaced with "K"; human Ig CH1 according to IMGT definition, ending with a conserved valine at IMGT position number 121):

```
Human CH1-EPKKAHIVMVDAYKPTKGAPHHHHHH
```

SEQ ID NO: 24 (Fab-Spy-His_ST4+2 (HC); partial amino acid sequence starting with the first 3 amino acid residues of the human IgG1 hinge domain and the fourth amino acid residue replaced with "S"; human Ig CH1 according to IMGT definition, ending with a conserved valine at IMGT position number 121):

```
Human CH1-EPKGAHIVMVDAYKPTKGAPHHHHHH
```

SEQ ID NO: 25 (Fab-Spy-His_ST4+3 (HC+1); partial amino acid sequence starting with the first 4 amino acid residues of the human IgG1 hinge domain; human Ig CH1 according to IMGT definition, ending with a conserved valine at IMGT position number 121):

```
Human CH1-EPKSDAHIVMVDAYKPTKGAPHHHHHH
```

SEQ ID NO: 26 (Fab-Spy-His_ST4+3 (HC+1); partial amino acid sequence starting with the first 4 amino acid residues of the human IgG1 hinge domain; human Ig CH1 according to IMGT definition, ending with a conserved valine at IMGT position number 121):

```
Human CH1-EPKSKAHIVMVDAYKPTKGAPHHHHHH
```

SEQ ID NO: 27 (Fab-Spy-His_ST4+3 (HC+1); partial amino acid sequence starting with the first 4 amino acid residues of the human IgG1 hinge domain; human Ig CH1 according to IMGT definition, ending with a conserved valine at IMGT position number 121):

```
Human CH1-EPKSPAHIVMVDAYKPTKGAPHHHHHH
```

SEQ ID NO: 28 (Fab-Spy-His_ST4+3 (HC+1); partial amino acid sequence starting with the first 4 amino acid residues of the human IgG1 hinge domain; human Ig CH1 according to IMGT definition, ending with a conserved valine at IMGT position number 121):

```
Human CH1-EPKSSAHIVMVDAYKPTKGAPHHHHHH
```

SEQ ID NO: 29 (Fab-Spy-His_ST4+4 (HC+2); partial amino acid sequence starting with the first 4 amino acid residues of the human IgG1 hinge domain; human Ig CH1 according to IMGT definition, ending with a conserved valine at IMGT position number 121):

```
Human CH1-
EPKSGGAHIVMVDAYKPTKGAPHHHHHH
```

SEQ ID NO: 30 (Fab-Spy-His_ST4+4 (HC+2); partial amino acid sequence starting with the first 4 amino acid residues of the human IgG1 hinge domain; human Ig CH1 according to IMGT definition, ending with a conserved valine at IMGT position number 121):

```
Human CH1-
EPKSGFAHIVMVDAYKPTKGAPHHHHHH
```

SEQ ID NO: 31 (Fab-Spy-His_ST4+5 (HC+3); partial amino acid sequence starting with the first 4 amino acid residues of the human IgG1 hinge domain; human Ig CH1 according to IMGT definition, ending with a conserved valine at IMGT position number 121):

```
Human CH1-
EPKSEGGAHIVMVDAYKPTKGAPHHHHHH
```

SEQ ID NO: 32
SEQ ID NO: 32 (Fab-Spy-His_ST4+5 (HC+3); partial amino acid sequence starting with the first 4 amino acid residues of the human IgG1 hinge domain; human Ig CH1 according to IMGT definition, ending with a conserved valine at IMGT position number 121):

```
Human CH1-
EPKSGGSAHIVMVDAYKPTKGAPHHHHHH
```

SEQ ID NO: 33 (MBP(Δ4aa)-Spy-His_ST4):

```
MKKTAIAIAVALAGFATVAQAKIEEGKLVIWINGDKGYNGLAEVGKKFEK

DTGIKVTVEHPDKLEEKFPQVAATGDGPDIIFWAHDRFGGYAQSGLLAEI

TPDKAFQDKLYPFTWDAVRYNGKLIAYPIAVEALSLIYNKDLLPNPPKTW

EEIPALDKELKAKGKSALMFNLQEPYFTWPLIAADGGYAFKYENGKYDIK

DVGVDNAGAKAGLTFLVDLIKNKHMNADTDYSIAEAAFNKGETAMTINGP

WAWSNIDTSKVNYGVTVLPTFKGQPSKPFVGVLSAGINAASPNKELAKEF

LENYLLTDEGLEAVNKDKPLGAVALKSYEEELAKDPRIAATMENAQKGEI

MPNIPQMSAFWYAVRTAVINAASGRQTVDEALKDAQTAHIVMVDAYKPTK

GAPHHHHHH
```

SEQ ID NO: 34 (scFv-F-Spy-H):

```
QVQLVESGGNLVQPGGSLRLSCAASGFTFGSFSMSWVRQAPGGGLEWVAG

LSARSSLTHYADSVKGRFTISRDNAKNSVYLQMNSLRVEDTAVYYCARRS

YDSSGYWGHFYSYMDVWGQGTLVTVSSGGGGSGGGGSGGGGSQSVLTQPS

SVSAAPGQKVTISCSGSTSNIGNNYVSWYQQHPGKAPKLMIYDVSKRPSG

VPDRFSGSKSGNSASLDISGLQSEDEADYYCAAWDDSLSEFLFGTGTKLT

VLGQEFDYKDDDDKGGSAHIVMVDAYKPTKGAPHHHHHH
```

SEQ ID NO: 35 (scFv(Δ6aa)-Spy-H):

```
QVQLVESGGNLVQPGGSLRLSCAASGFTFGSFSMSWVRQAPGGGLEWVAG

LSARSSLTHYADSVKGRFTISRDNAKNSVYLQMNSLRVEDTAVYYCARRS

YDSSGYWGHFYSYMDVWGQGTLVTVSSGGGGSGGGGSGGGGSQSVLTQPS

SVSAAPGQKVTISCSGSTSNIGNNYVSWYQQHPGKAPKLMIYDVSKRPSG

VPDRFSGSKSGNSASLDISGLQSEDEADYYCAAWDDSLSEFLFGTGTKAH

IVMVDAYKPTKGAPHHHHHH
```

SEQ ID NO: 36 (SpyTag003)

```
RGVPHIVMVDAYKRYK
```

REFERENCES

U.S. Pat. No. 9,547,003
U.S. Patent Application No: 2003/0198956
WO 2016/193746
WO 2016/183387
WO 2018/053180
IMGT definitions according to Lefranc M.-P., De R K, Tomar N. Immunoinformatics of the V, C and G domains: IMGT® definitive system for IG, TR and IgSF, MH and MhSF, Immunoinformatics: From Biology to Informatics, 2014, vol. 1184 2nd edition Springer, N.Y. Humana Press (pg. 59-107).
Abe, H., Rie, W., Yonemura, H., Yamada, S., Goto, M., and Kamiya, N., (2013), Split Spy0128 as a Potent Scaffold for Protein Cross-Linking and Immobilization. Bioconjugate Chem., 24(2), 242-250.
Alam et al., 2017, Synthetic Modular Antibody Construction Using the SpyTag/SpyCatcher Protein Ligase System. Chembiochem. 18(22), 2217-2221.
Alves, N. J., Turner, K. B., Daniele, M. A., Oh, E., Medintz, I. L., Walper, S. A., Bacterial nanobioreactors-directing enzyme packaging into bacterial outer membrane vesicles. ACS Appl Mater Interfaces, 2015; 7: 24963-24972.
Berman H M, Westbrook J, Feng Z, Gilliland G, Bhat T N, Weissig H, Shindyalov I N, Bourne PE., 2000, The Protein Data Bank. Nucleic Acids Res. 28(1), 235-42.

Brannon, J. R., Burk, D. L., Leclerc, J. M., Thomassin, J. L., Portt, A., Berghuis, A. M., Gruenheid, S., Le Moual H., 2015, Inhibition of outer membrane proteases of the omptin family by aprotinin. Infect Immun., 83:2300-2311.

Buldun, C. M., Jean, J., Bedford, M. R., Howarth, M., 2018, SnoopLigase catalyzes peptide-peptide locking and enables solid-phase conjugate isolation. J Am Chem Soc. 140(8), 3008-3018.

Datsenko, K. A. and Wanner, B. L., 2000, One-step inactivation of chromosomal genes in Escherichia coli K-12 using PCR products. Proc Natl Acad Sci USA. 97 (12), 6640-6645.

Ezkurdia I, Tress ML., 2011, Protein structural domains: definition and prediction. Curr Protoc Protein Sci. Chapter 2:Unit2.14. doi: 10.1002/0471140864.ps0214s66.

Fierer, J. O., Veggiani, G., Howarth, M., 2014, SpyLigase peptide-peptide ligation polymerizes affibodies to enhance magnetic cancer cell capture. Proc Natl Acad Sci USA. 111:E1176-1181.

Geller, B. L., 2005, Antibacterial antisense. Curr Opin Mol Ther, 7:109-113.

Keeble, A. H., Banerjee, A., Ferla, M. P., Reddington, S. C., Khairil Anuar, I. N. A., Howarth, M., 2017, Evolving accelerated amidation by SpyTag/SpyCatcher to analyze membrane dynamics. Ange, Chem. Int. Ed. 56:16521-16525.

Keeble, A. H., Howarth, M., 2019, Insider information on successful covalent protein coupling with help from SpyBank. Methods in Enzymology. 617: 443-461. doi.org/10.1016/bs.mie.2018.12.010.

Keeble, A. H., Turkki, P., Stokes, S., Khairil Anuar, I. N. A., Rahikainen, R., Hytonen, V. P., Howarth, M., 2019, Approaching infinite affinity through engineering of peptide-protein interaction. Proc Natl Acad Sci USA. 116: 26526-26533.

Keiler, K. and Sauer, R., 1995, Identification of Active Site Residues of the Tsp Protease. J Biol Chem, 270 (48), 28864-28868.

Knappik, A., Brundiers, R., 2009, Recombinant antibody expression and purification, In: Walker, J. M. editor. The Protein Protocols Handbook. 3rd edition. New York: Humana Press Inc., 1929-1943.

Li et al., 2014, Structural analysis and optimization of the covalent association between SpyCatcher and a peptide Tag, J Mol Biol. 426(2), 309-17.

Nguyen, G. K. T., Wang, S., Qiu, Y., Hemu, X., Lian, Y., Tam, J. P., 2014, Butelase 1 is an Asx-specific ligase enabling peptide macrocyclization and synthesis. Nat Chem Biol. 10:732-738.

Plückthun A., 1990, Antibodies from Escherichia coli. Nature 347, 497-498.

Prouty, W. F., Goldberg, A. L., 1972, Effects of protease inhibitors on protein breakdown in Escherichia coli. J Biol Chem, 247:3341-3352.

Qi, F. et al., 2018, Evolutionary analysis of polyproline motifs in Escherichia coli reveals their regulatory role in translation. PLoS Comput Biol. 14(2), e1005987.

Reddington, S. C., Howarth, M., 2015, Secrets of a covalent interaction for biomaterials and biotechnology: SpyTag and SpyCatcher. Current Opinion in Chemical Biology. 29:94-99.

Schmohl, L., Schwarzer, D., 2014, Sortase-mediated ligations for the site-specific modification of proteins. Current Opinion in Chemical Biology. 22:122-128.

Siegmund et al., 2016, Spontaneous Isopeptide Bond Formation as a Powerful Tool for Engineering Site-Specific Antibody-Drug Conjugates. Scientific Reports. 6, 39291.

Silber, K. R., Keiler, K. C., Sauer, R. T., 1991, Tsp: A tail-specific protease that selectively degrades proteins with nonpolar C termini. Proc Natl Acad Sci USA, 89:295-299.

Tan et al. (2016). Kinetic Controlled Tag-Catcher Interactions for Directed Covalent Protein Assembly. PLoS ONE, 11(10), e0165074.

Toplak, A., Nuljens, T., Quaedflieg, P. J. L., Wu, B., Janssen, D. B., 2016, Peptiligase, an enzyme foe efficient chemoenzymatic peptide synthesis and cyclization in water. Adv Synth Catal. 358:32140-32147.

Veggiani, G. et al., 2016, Programmable polyproteams built using twin peptide superglues. Proc Natl Acad Sci USA 113:1202-1207.

Waugh, D. S., 2016, Crystal structures of MBP fusion proteins. Protein Sci. 25:559-571.

Wu, C., Leroux, J. C., Gauthier, M. A., 2012, Twin disulfides for orthogonal disulfide pairing and the directed folding of multicyclic peptides. Nat Chem. 4:1044-1049.

Yumura, K. et al., 2017, Use of SpyTag/SpyCatcher to construct bispecific antibodies that target two epitopes of a single antigen. J Biochem. 162(3), 203-210.

Zakeri, B. et al., 2012, Peptide tag forming a rapid covalent bond to a protein, through engineering a bacterial adhesion. Proc Natl Acad Sci USA. 109:E690-697.

The invention claimed is:

1. A method for producing a periplasmic fusion protein, the method comprising:
   culturing *E. coli* host cells transformed with a vector containing nucleic acid encoding the periplasmic fusion protein in a culture medium under conditions effective to express the periplasmic fusion protein, wherein:
   the periplasmic fusion protein comprises a binding motif attached to a first protein or embedded within an amino acid sequence of the first protein;
   the binding motif comprises SEQ ID NO: 1 or a sequence with at least 60% sequence identity to SEQ ID NO: 1; and
   the *E. coli* host cells have reduced or no tail-specific protease (Tsp) protein activity as compared to a wild-type cell resulting from:
   a) a mutation in the Tsp gene that encodes a mutated Tsp protein and the mutation reduces or eliminates protease activity; or
   b) a mutation in the Tsp gene or regulatory sequence of the Tsp gene that reduces or eliminates expression of the Tsp protein; or
   c) one or more deletions of regions in the bacterial chromosome that reduces or eliminates Tsp protein activity; or
   d) an inhibitor or inactivator that reduces or eliminates Tsp protease activity or an inhibitor of Tsp protease expression; and
   recovering the periplasmic fusion protein from the *E. coli* host cells.

2. A method for producing a periplasmic fusion protein, the method comprising:
   culturing *E. coli* host cells transformed with a vector containing nucleic acid encoding the periplasmic fusion protein in a culture medium under conditions effective to express the periplasmic fusion protein, wherein:
   the periplasmic fusion protein comprises a binding motif attached to a first protein or embedded within an amino acid sequence of the first protein;
   the binding motif comprises SEQ ID NO: 2 or a sequence with at least 70% sequence identity to SEQ ID NO: 2 or SEQ ID NO: 36 or a sequence with at least 78% sequence identity to SEQ ID NO: 36; and
   the *E. coli* host cells have reduced or no Tsp protein activity and ompT protein activity as compared to a wild-type cell resulting from:
   a) a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity; and
   b) a mutation in the ompT gene that encodes a mutated ompT protein and the mutation reduces or eliminates protease activity, or a mutation in the ompT gene or regulatory sequence of the ompT gene that reduces or eliminates expression of the ompT protein, or one or more deletions of regions in the bacterial chromosome that reduces or eliminates ompT protein activity; and
   recovering the periplasmic fusion protein from the *E. coli* host cells.

3. A method for producing a periplasmic fusion protein, the method comprising:
   culturing *E. coli* host cells transformed with a vector containing nucleic acid encoding the periplasmic fusion protein in a culture medium under conditions effective to express the periplasmic fusion protein, wherein:

the periplasmic fusion protein comprises a binding motif attached to a first protein or embedded within an amino acid sequence of the first protein;

the binding motif comprises SEQ ID NO: 2 or a sequence with at least 70% sequence identity to SEQ ID NO: 2 or SEQ ID NO: 36 or a sequence with at least 78% sequence identity to SEQ ID NO: 36; and the *E. coli* host cells have reduced or no Tsp protease activity and ompT protease activity as compared to a wild-type cell resulting from:

a) an inhibitor or inactivator of Tsp protease or an inhibitor of Tsp expression; and b) an inhibitor or inactivator of ompT protease or an inhibitor of ompT expression; and recovering the periplasmic fusion protein from the *E. coli* host cells.

4. The method of claim 1, wherein the binding motif is attached directly or via a linker sequence to the C terminus of the first protein.

5. The method of claim 1, wherein the first protein is an antigen binding fragment and the antigen binding fragment comprises a Fab, scFv, or scFab.

6. The method of claim 5, wherein the antigen binding fragment is a Fab.

7. The method of claim 1, wherein the *E. coli* host cells are a mutant *E. coli* TG1 F- strain having DSM accession number 33004, deposited on Jan. 8, 2019.

8. The method of claim 2, wherein the *E. coli* host cells are a mutant *E. coli* TG1 F- strain having DSM accession number 33005, deposited on Jan. 8, 2019.

9. An *E. coli* TG1, TG1 F-, XL1 Blue, MC1061, SS320, BL21, JM83, JM109, HB2151, W3110, or Cmax5 alpha strain comprising a nucleic acid encoding a periplasmic fusion protein comprising a binding motif and the binding motif comprises SEQ ID NO: 1 or a sequence with at least 60% sequence identity to SEQ ID NO: 1, wherein the *E. coli* strain has reduced or no Tsp protein activity as compared to a wild-type cell resulting from a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity.

10. An *E. coli* TG1, TG1 F-, XL1 Blue, MC1061, SS320, BL21, JM83, JM109, HB2151, W3110, or Cmax5 alpha strain comprising:

a) a nucleic acid encoding a periplasmic fusion protein comprising a binding motif and the binding motif comprises SEQ ID NO: 2 or a sequence with at least 70% sequence identity to SEQ ID NO: 2; or b) a nucleic acid encoding a periplasmic fusion protein comprising a binding motif and the binding motif comprises SEQ ID NO: 36 or a sequence with at least 78% sequence identity to SEQ ID NO: 36, wherein the *E. coli* strain has reduced or no Tsp protein activity and ompT protein activity as compared to a wild-type cell resulting from:

a) a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity; and b) a mutation in the ompT gene that encodes a mutated ompT protein and the mutation reduces or eliminates protease activity, or a mutation in the ompT gene or regulatory sequence of the ompT gene that reduces or eliminates expression of the ompT protein, or one or more deletions of regions in the bacterial chromosome that reduces or eliminates ompT protein activity.

11. A mutant *E. coli* strain:

a) having reduced or no Tsp protein activity as compared to a wild-type cell resulting from a mutation in the Tsp gene that encodes a mutated Tsp protein and the mutation reduces or eliminates protease activity, or a mutation in the Tsp gene or regulatory sequence of the Tsp gene that reduces or eliminates expression of the Tsp protein, or one or more deletions of regions in the bacterial chromosome that reduces or eliminates Tsp protein activity;

for the expression of periplasmic fusion protein comprising a binding motif attached to a first protein or embedded within an amino acid sequence of the first protein; the binding motif comprises SEQ ID NO: 1 or a sequence with at least 60% sequence identity to SEQ ID NO: 1; or b) having reduced or no Tsp protein activity and ompT protein activity as compared to a wild-type cell resulting from:

i) a mutation in the Tsp gene that encodes a mutated Tsp protein and that reduces or eliminates protease activity, or a mutation in the Tsp gene or regulatory sequence of the Tsp gene that reduces or eliminates expression of the Tsp protein, or one or more deletions of regions in the bacterial chromosome that reduce or eliminate Tsp protein activity; and ii) a mutation in the ompT gene that encodes a mutated ompT protein and that reduces or eliminates protease activity, or a mutation in the ompT gene or regulatory sequence of the ompT gene that reduces or eliminates expression of the ompT protein, or one or more deletions of regions in the bacterial chromosome that reduces or eliminates ompT protein activity;

for the expression of periplasmic fusion protein comprising a binding motif attached to a first protein or embedded within an amino acid sequence of the first protein; the binding motif comprises SEQ ID NO: 2 or SEQ ID NO: 36 or a sequence with at least 70% sequence identity to SEQ ID NO: 2 or at least 78% sequence identity to SEQ ID NO: 36, respectively.

12. A mutant *E. coli* TG1 F- strain having DSM accession number 33004 or 33005, both deposited on Jan. 8, 2019.

13. The method of claim 1 wherein the periplasmic fusion protein comprises a binding motif attached directly or via a linker to a C-terminus of a protein structural domain in a first protein, wherein the binding motif comprises SEQ ID NO: 1 or a sequence with at least 60% sequence identity to SEQ ID NO :1.

14. The method of claim 13 wherein the binding motif of the periplasmic fusion protein is attached directly to the C-terminus of the protein structural domain in the first protein and the binding motif is proteolytically resistant.

15. The method of claim 14 comprising the periplasmic fusion protein, wherein the protein structural domain is a human scFv single chain antibody fragment that is C-terminally truncated within the FR4 region.

16. The method of claim 13 wherein the binding motif of the periplasmic fusion protein, is attached to the C-terminus of the protein structural domain in the first protein via a 1 or 2 amino acid linker.

17. The method of claim 13 wherein the binding motif of the periplasmic fusion protein is attached to the C-terminus at IMGT position 121 of a human heavy chain CH1 antibody domain via a 2, 3, or 4 amino acid linker.

18. The method of claim 13 wherein the binding motif of the periplasmic fusion protein is attached to the C-terminus at IMGT position 121 of a human constant light chain antibody domain via a 2, 3, or 4 amino acid linker.

19. The method of claim 13 wherein the nucleic acid construct comprises a polynucleotide sequence encoding the periplasmic fusion protein.

20. A method wherein the vector comprises the nucleic acid construct of claim 19.

* * * * *

SEQUENCE LISTING

<160> NUMBER OF SEQ ID NOS: 36

<210> SEQ ID NO 1
<211> LENGTH: 13
<212> TYPE: PRT
<213> ORGANISM: Artificial Sequence
<220> FEATURE:
<223> OTHER INFORMATION: synthetic

<400> SEQUENCE: 1

Ala His Ile Val Met Val Asp Ala Tyr Lys Pro Thr Lys
1               5                   10

<210> SEQ ID NO 2
<211> LENGTH: 14
<212> TYPE: PRT
<213> ORGANISM: Artificial Sequence

```
<220> FEATURE:
<223> OTHER INFORMATION: synthetic

<400> SEQUENCE: 2

Val Pro Thr Ile Val Met Val Asp Ala Tyr Lys Arg Tyr Lys
1               5                   10

<210> SEQ ID NO 3
<211> LENGTH: 29
<212> TYPE: PRT
<213> ORGANISM: Artificial Sequence
<220> FEATURE:
<223> OTHER INFORMATION: synthetic

<400> SEQUENCE: 3

Glu Pro Lys Ser Glu Phe Gly Ala His Ile Val Met Val Asp Ala Tyr
1               5                   10                  15

Lys Pro Thr Lys Gly Ala Pro His His His His His
            20                  25

<210> SEQ ID NO 4
<211> LENGTH: 39
<212> TYPE: PRT
<213> ORGANISM: Artificial Sequence
<220> FEATURE:
<223> OTHER INFORMATION: synthetic

<400> SEQUENCE: 4

Glu Pro Lys Ser Glu Phe Asp Tyr Lys Asp Asp Asp Lys Gly Gly
1               5                   10                  15

Ser Ala His Ile Val Met Val Asp Ala Tyr Lys Pro Thr Lys Gly Ala
                20                  25                  30

Pro His His His His His His
        35

<210> SEQ ID NO 5
<211> LENGTH: 36
<212> TYPE: PRT
<213> ORGANISM: Artificial Sequence
<220> FEATURE:
<223> OTHER INFORMATION: synthetic

<400> SEQUENCE: 5

Glu Pro Lys Ser Glu Phe Gly Gly Gly Ser Gly Gly Gly Ser Ala His
1               5                   10                  15

Ile Val Met Val Asp Ala Tyr Lys Pro Thr Lys Gly Ala Pro His His
                20                  25                  30

His His His His
        35

<210> SEQ ID NO 6
<211> LENGTH: 29
<212> TYPE: PRT
<213> ORGANISM: Artificial Sequence
<220> FEATURE:
<223> OTHER INFORMATION: synthetic

<400> SEQUENCE: 6

Glu Pro Lys Ser Glu Phe His His His His His Gly Ala Pro Gly
1               5                   10                  15

Ala His Ile Val Met Val Asp Ala Tyr Lys Pro Thr Lys
            20                  25
```

```
<210> SEQ ID NO 7
<211> LENGTH: 40
<212> TYPE: PRT
<213> ORGANISM: Artificial Sequence
<220> FEATURE:
<223> OTHER INFORMATION: synthetic

<400> SEQUENCE: 7

Glu Pro Lys Ser Glu Phe His His His His His Gly Ala Pro Gly
1               5                   10                  15

Ala His Ile Val Met Val Asp Ala Tyr Lys Pro Thr Lys Gly Gly Ser
            20                  25                  30

Asp Tyr Lys Asp Asp Asp Lys
        35                  40

<210> SEQ ID NO 8
<211> LENGTH: 53
<212> TYPE: PRT
<213> ORGANISM: Artificial Sequence
<220> FEATURE:
<223> OTHER INFORMATION: synthetic

<400> SEQUENCE: 8

Glu Pro Lys Ser Glu Phe Gly Ala His Ile Val Met Val Asp Ala Tyr
1               5                   10                  15

Lys Pro Thr Lys Gly Ala Pro Ser Ala Trp Ser His Pro Gln Phe Glu
            20                  25                  30

Lys Gly Gly Gly Ser Gly Gly Gly Ser Ala Trp Ser His
        35                  40                  45

Pro Gln Phe Glu Lys
    50

<210> SEQ ID NO 9
<211> LENGTH: 63
<212> TYPE: PRT
<213> ORGANISM: Artificial Sequence
<220> FEATURE:
<223> OTHER INFORMATION: synthetic

<400> SEQUENCE: 9

Glu Pro Lys Ser Glu Phe Asp Tyr Lys Asp Asp Asp Lys Gly Gly
1               5                   10                  15

Ser Ala His Ile Val Met Val Asp Ala Tyr Lys Pro Thr Lys Gly Ala
            20                  25                  30

Pro Ser Ala Trp Ser His Pro Gln Phe Glu Lys Gly Gly Gly Ser Gly
        35                  40                  45

Gly Gly Ser Gly Gly Ser Ala Trp Ser His Pro Gln Phe Glu Lys
    50                  55                  60

<210> SEQ ID NO 10
<211> LENGTH: 60
<212> TYPE: PRT
<213> ORGANISM: Artificial Sequence
<220> FEATURE:
<223> OTHER INFORMATION: synthetic

<400> SEQUENCE: 10

Glu Pro Lys Ser Glu Phe Gly Gly Gly Ser Gly Gly Gly Ser Ala His
1               5                   10                  15

Ile Val Met Val Asp Ala Tyr Lys Pro Thr Lys Gly Ala Pro Ser Ala
            20                  25                  30
```

```
Trp Ser His Pro Gln Phe Glu Lys Gly Gly Gly Ser Gly Gly Gly Ser
        35                  40                  45

Gly Gly Ser Ala Trp Ser His Pro Gln Phe Glu Lys
    50                  55                  60

<210> SEQ ID NO 11
<211> LENGTH: 422
<212> TYPE: PRT
<213> ORGANISM: Artificial Sequence
<220> FEATURE:
<223> OTHER INFORMATION: synthetic

<400> SEQUENCE: 11

Met Lys Lys Thr Ala Ile Ala Ile Ala Val Ala Leu Ala Gly Phe Ala
1               5                   10                  15

Thr Val Ala Gln Ala Lys Ile Glu Glu Gly Lys Leu Val Ile Trp Ile
            20                  25                  30

Asn Gly Asp Lys Gly Tyr Asn Gly Leu Ala Glu Val Gly Lys Lys Phe
        35                  40                  45

Glu Lys Asp Thr Gly Ile Lys Val Thr Val Glu His Pro Asp Lys Leu
    50                  55                  60

Glu Glu Lys Phe Pro Gln Val Ala Ala Thr Gly Asp Gly Pro Asp Ile
65                  70                  75                  80

Ile Phe Trp Ala His Asp Arg Phe Gly Gly Tyr Ala Gln Ser Gly Leu
                85                  90                  95

Leu Ala Glu Ile Thr Pro Asp Lys Ala Phe Gln Asp Lys Leu Tyr Pro
            100                 105                 110

Phe Thr Trp Asp Ala Val Arg Tyr Asn Gly Lys Leu Ile Ala Tyr Pro
        115                 120                 125

Ile Ala Val Glu Ala Leu Ser Leu Ile Tyr Asn Lys Asp Leu Leu Pro
    130                 135                 140

Asn Pro Pro Lys Thr Trp Glu Glu Ile Pro Ala Leu Asp Lys Glu Leu
145                 150                 155                 160

Lys Ala Lys Gly Lys Ser Ala Leu Met Phe Asn Leu Gln Glu Pro Tyr
                165                 170                 175

Phe Thr Trp Pro Leu Ile Ala Ala Asp Gly Gly Tyr Ala Phe Lys Tyr
            180                 185                 190

Glu Asn Gly Lys Tyr Asp Ile Lys Asp Val Gly Val Asp Asn Ala Gly
        195                 200                 205

Ala Lys Ala Gly Leu Thr Phe Leu Val Asp Leu Ile Lys Asn Lys His
    210                 215                 220

Met Asn Ala Asp Thr Asp Tyr Ser Ile Ala Glu Ala Ala Phe Asn Lys
225                 230                 235                 240

Gly Glu Thr Ala Met Thr Ile Asn Gly Pro Trp Ala Trp Ser Asn Ile
                245                 250                 255

Asp Thr Ser Lys Val Asn Tyr Gly Val Thr Val Leu Pro Thr Phe Lys
            260                 265                 270

Gly Gln Pro Ser Lys Pro Phe Val Gly Val Leu Ser Ala Gly Ile Asn
        275                 280                 285

Ala Ala Ser Pro Asn Lys Glu Leu Ala Lys Glu Phe Leu Glu Asn Tyr
    290                 295                 300

Leu Leu Thr Asp Glu Gly Leu Glu Ala Val Asn Lys Asp Lys Pro Leu
305                 310                 315                 320

Gly Ala Val Ala Leu Lys Ser Tyr Glu Glu Glu Leu Ala Lys Asp Pro
                325                 330                 335
```

```
Arg Ile Ala Ala Thr Met Glu Asn Ala Gln Lys Gly Glu Ile Met Pro
                340                 345                 350

Asn Ile Pro Gln Met Ser Ala Phe Trp Tyr Ala Val Arg Thr Ala Val
            355                 360                 365

Ile Asn Ala Ala Ser Gly Arg Gln Thr Val Asp Glu Ala Leu Lys Asp
        370                 375                 380

Ala Gln Thr Glu Phe Asp Tyr Lys Asp Asp Asp Lys Gly Gly Ser
385                 390                 395                 400

Ala His Ile Val Met Val Asp Ala Tyr Lys Pro Thr Lys Gly Ala Pro
                405                 410                 415

His His His His His His
            420
```

<210> SEQ ID NO 12
<211> LENGTH: 423
<212> TYPE: PRT
<213> ORGANISM: Artificial Sequence
<220> FEATURE:
<223> OTHER INFORMATION: synthetic

<400> SEQUENCE: 12

```
Met Lys Lys Thr Ala Ile Ala Ile Ala Val Ala Leu Ala Gly Phe Ala
1               5                   10                  15

Thr Val Ala Gln Ala Lys Ile Glu Glu Gly Lys Leu Val Ile Trp Ile
            20                  25                  30

Asn Gly Asp Lys Gly Tyr Asn Gly Leu Ala Glu Val Gly Lys Lys Phe
        35                  40                  45

Glu Lys Asp Thr Gly Ile Lys Val Thr Val Glu His Pro Asp Lys Leu
50                  55                  60

Glu Glu Lys Phe Pro Gln Val Ala Ala Thr Gly Asp Gly Pro Asp Ile
65                  70                  75                  80

Ile Phe Trp Ala His Asp Arg Phe Gly Gly Tyr Ala Gln Ser Gly Leu
                85                  90                  95

Leu Ala Glu Ile Thr Pro Asp Lys Ala Phe Gln Asp Lys Leu Tyr Pro
            100                 105                 110

Phe Thr Trp Asp Ala Val Arg Tyr Asn Gly Lys Leu Ile Ala Tyr Pro
        115                 120                 125

Ile Ala Val Glu Ala Leu Ser Leu Ile Tyr Asn Lys Asp Leu Leu Pro
130                 135                 140

Asn Pro Pro Lys Thr Trp Glu Glu Ile Pro Ala Leu Asp Lys Glu Leu
145                 150                 155                 160

Lys Ala Lys Gly Lys Ser Ala Leu Met Phe Asn Leu Gln Glu Pro Tyr
                165                 170                 175

Phe Thr Trp Pro Leu Ile Ala Ala Asp Gly Gly Tyr Ala Phe Lys Tyr
            180                 185                 190

Glu Asn Gly Lys Tyr Asp Ile Lys Asp Val Gly Val Asp Asn Ala Gly
        195                 200                 205

Ala Lys Ala Gly Leu Thr Phe Leu Val Asp Leu Ile Lys Asn Lys His
210                 215                 220

Met Asn Ala Asp Thr Asp Tyr Ser Ile Ala Glu Ala Ala Phe Asn Lys
225                 230                 235                 240

Gly Glu Thr Ala Met Thr Ile Asn Gly Pro Trp Ala Trp Ser Asn Ile
                245                 250                 255

Asp Thr Ser Lys Val Asn Tyr Gly Val Thr Val Leu Pro Thr Phe Lys
            260                 265                 270
```

Gly Gln Pro Ser Lys Pro Phe Val Gly Val Leu Ser Ala Gly Ile Asn
            275                 280                 285

Ala Ala Ser Pro Asn Lys Glu Leu Ala Lys Glu Phe Leu Glu Asn Tyr
        290                 295                 300

Leu Leu Thr Asp Glu Gly Leu Glu Ala Val Asn Lys Asp Lys Pro Leu
305                 310                 315                 320

Gly Ala Val Ala Leu Lys Ser Tyr Glu Glu Leu Ala Lys Asp Pro
                325                 330                 335

Arg Ile Ala Ala Thr Met Glu Asn Ala Gln Lys Gly Glu Ile Met Pro
                340                 345                 350

Asn Ile Pro Gln Met Ser Ala Phe Trp Tyr Ala Val Arg Thr Ala Val
            355                 360                 365

Ile Asn Ala Ala Ser Gly Arg Gln Thr Val Asp Glu Ala Leu Lys Asp
        370                 375                 380

Ala Gln Thr Glu Phe His His His His His His Gly Ala Pro Gly Ala
385                 390                 395                 400

His Ile Val Met Val Asp Ala Tyr Lys Pro Thr Lys Gly Gly Ser Asp
                405                 410                 415

Tyr Lys Asp Asp Asp Asp Lys
            420

<210> SEQ ID NO 13
<211> LENGTH: 30
<212> TYPE: PRT
<213> ORGANISM: Artificial Sequence
<220> FEATURE:
<223> OTHER INFORMATION: synthetic

<400> SEQUENCE: 13

Glu Pro Lys Ser Glu Phe Gly Val Pro Thr Ile Val Met Val Asp Ala
1               5                   10                  15

Tyr Lys Arg Tyr Lys Gly Ala Pro His His His His His His
            20                  25                  30

<210> SEQ ID NO 14
<211> LENGTH: 40
<212> TYPE: PRT
<213> ORGANISM: Artificial Sequence
<220> FEATURE:
<223> OTHER INFORMATION: synthetic

<400> SEQUENCE: 14

Glu Pro Lys Ser Glu Phe Asp Tyr Lys Asp Asp Asp Lys Gly Gly
1               5                   10                  15

Ser Val Pro Thr Ile Val Met Val Asp Ala Tyr Lys Arg Tyr Lys Gly
            20                  25                  30

Ala Pro His His His His His His
        35                  40

<210> SEQ ID NO 15
<211> LENGTH: 30
<212> TYPE: PRT
<213> ORGANISM: Artificial Sequence
<220> FEATURE:
<223> OTHER INFORMATION: synthetic

<400> SEQUENCE: 15

Glu Pro Lys Ser Glu Phe His His His His His Gly Ala Pro Gly
1               5                   10                  15

```
Val Pro Thr Ile Val Met Val Asp Ala Tyr Lys Arg Tyr Lys
            20                  25                  30
```

```
<210> SEQ ID NO 16
<211> LENGTH: 24
<212> TYPE: PRT
<213> ORGANISM: Artificial Sequence
<220> FEATURE:
<223> OTHER INFORMATION: synthetic

<400> SEQUENCE: 16

Glu Pro Ala His Ile Val Met Val Asp Ala Tyr Lys Pro Thr Lys Gly
1               5                   10                  15

Ala Pro His His His His His His
            20
```

```
<210> SEQ ID NO 17
<211> LENGTH: 25
<212> TYPE: PRT
<213> ORGANISM: Artificial Sequence
<220> FEATURE:
<223> OTHER INFORMATION: synthetic

<400> SEQUENCE: 17

Glu Pro Lys Ala His Ile Val Met Val Asp Ala Tyr Lys Pro Thr Lys
1               5                   10                  15

Gly Ala Pro His His His His His His
            20                  25
```

```
<210> SEQ ID NO 18
<211> LENGTH: 25
<212> TYPE: PRT
<213> ORGANISM: Artificial Sequence
<220> FEATURE:
<223> OTHER INFORMATION: synthetic

<400> SEQUENCE: 18

Glu Pro Glu Ala His Ile Val Met Val Asp Ala Tyr Lys Pro Thr Lys
1               5                   10                  15

Gly Ala Pro His His His His His His
            20                  25
```

```
<210> SEQ ID NO 19
<211> LENGTH: 25
<212> TYPE: PRT
<213> ORGANISM: Artificial Sequence
<220> FEATURE:
<223> OTHER INFORMATION: synthetic

<400> SEQUENCE: 19

Glu Pro Gly Ala His Ile Val Met Val Asp Ala Tyr Lys Pro Thr Lys
1               5                   10                  15

Gly Ala Pro His His His His His His
            20                  25
```

```
<210> SEQ ID NO 20
<211> LENGTH: 25
<212> TYPE: PRT
<213> ORGANISM: Artificial Sequence
<220> FEATURE:
<223> OTHER INFORMATION: synthetic

<400> SEQUENCE: 20

Glu Pro Arg Ala His Ile Val Met Val Asp Ala Tyr Lys Pro Thr Lys
1               5                   10                  15
```

Gly Ala Pro His His His His His His
            20                  25

<210> SEQ ID NO 21
<211> LENGTH: 26
<212> TYPE: PRT
<213> ORGANISM: Artificial Sequence
<220> FEATURE:
<223> OTHER INFORMATION: synthetic

<400> SEQUENCE: 21

Glu Pro Lys Ser Ala His Ile Val Met Val Asp Ala Tyr Lys Pro Thr
1               5                   10                  15

Lys Gly Ala Pro His His His His His His
            20                  25

<210> SEQ ID NO 22
<211> LENGTH: 26
<212> TYPE: PRT
<213> ORGANISM: Artificial Sequence
<220> FEATURE:
<223> OTHER INFORMATION: synthetic

<400> SEQUENCE: 22

Glu Pro Lys Glu Ala His Ile Val Met Val Asp Ala Tyr Lys Pro Thr
1               5                   10                  15

Lys Gly Ala Pro His His His His His His
            20                  25

<210> SEQ ID NO 23
<211> LENGTH: 26
<212> TYPE: PRT
<213> ORGANISM: Artificial Sequence
<220> FEATURE:
<223> OTHER INFORMATION: synthetic

<400> SEQUENCE: 23

Glu Pro Lys Lys Ala His Ile Val Met Val Asp Ala Tyr Lys Pro Thr
1               5                   10                  15

Lys Gly Ala Pro His His His His His His
            20                  25

<210> SEQ ID NO 24
<211> LENGTH: 26
<212> TYPE: PRT
<213> ORGANISM: Artificial Sequence
<220> FEATURE:
<223> OTHER INFORMATION: synthetic

<400> SEQUENCE: 24

Glu Pro Lys Gly Ala His Ile Val Met Val Asp Ala Tyr Lys Pro Thr
1               5                   10                  15

Lys Gly Ala Pro His His His His His His
            20                  25

<210> SEQ ID NO 25
<211> LENGTH: 27
<212> TYPE: PRT
<213> ORGANISM: Artificial Sequence
<220> FEATURE:
<223> OTHER INFORMATION: synthetic

<400> SEQUENCE: 25

Glu Pro Lys Ser Asp Ala His Ile Val Met Val Asp Ala Tyr Lys Pro
1               5                   10                  15

Thr Lys Gly Ala Pro His His His His His His
            20                  25

<210> SEQ ID NO 26
<211> LENGTH: 27
<212> TYPE: PRT
<213> ORGANISM: Artificial Sequence
<220> FEATURE:
<223> OTHER INFORMATION: synthetic

<400> SEQUENCE: 26

Glu Pro Lys Ser Lys Ala His Ile Val Met Val Asp Ala Tyr Lys Pro
1               5                   10                  15

Thr Lys Gly Ala Pro His His His His His His
            20                  25

<210> SEQ ID NO 27
<211> LENGTH: 27
<212> TYPE: PRT
<213> ORGANISM: Artificial Sequence
<220> FEATURE:
<223> OTHER INFORMATION: synthetic

<400> SEQUENCE: 27

Glu Pro Lys Ser Pro Ala His Ile Val Met Val Asp Ala Tyr Lys Pro
1               5                   10                  15

Thr Lys Gly Ala Pro His His His His His His
            20                  25

<210> SEQ ID NO 28
<211> LENGTH: 27
<212> TYPE: PRT
<213> ORGANISM: Artificial Sequence
<220> FEATURE:
<223> OTHER INFORMATION: synthetic

<400> SEQUENCE: 28

Glu Pro Lys Ser Ser Ala His Ile Val Met Val Asp Ala Tyr Lys Pro
1               5                   10                  15

Thr Lys Gly Ala Pro His His His His His His
            20                  25

<210> SEQ ID NO 29
<211> LENGTH: 28
<212> TYPE: PRT
<213> ORGANISM: Artificial Sequence
<220> FEATURE:
<223> OTHER INFORMATION: synthetic

<400> SEQUENCE: 29

Glu Pro Lys Ser Gly Gly Ala His Ile Val Met Val Asp Ala Tyr Lys
1               5                   10                  15

Pro Thr Lys Gly Ala Pro His His His His His His
            20                  25

<210> SEQ ID NO 30
<211> LENGTH: 28
<212> TYPE: PRT
<213> ORGANISM: Artificial Sequence
<220> FEATURE:

```
<223> OTHER INFORMATION: synthetic

<400> SEQUENCE: 30

Glu Pro Lys Ser Gly Phe Ala His Ile Val Met Val Asp Ala Tyr Lys
1               5                   10                  15

Pro Thr Lys Gly Ala Pro His His His His His
            20                  25

<210> SEQ ID NO 31
<211> LENGTH: 29
<212> TYPE: PRT
<213> ORGANISM: Artificial Sequence
<220> FEATURE:
<223> OTHER INFORMATION: synthetic

<400> SEQUENCE: 31

Glu Pro Lys Ser Glu Gly Gly Ala His Ile Val Met Val Asp Ala Tyr
1               5                   10                  15

Lys Pro Thr Lys Gly Ala Pro His His His His His
            20                  25

<210> SEQ ID NO 32
<211> LENGTH: 29
<212> TYPE: PRT
<213> ORGANISM: Artificial Sequence
<220> FEATURE:
<223> OTHER INFORMATION: synthetic

<400> SEQUENCE: 32

Glu Pro Lys Ser Gly Gly Ser Ala His Ile Val Met Val Asp Ala Tyr
1               5                   10                  15

Lys Pro Thr Lys Gly Ala Pro His His His His His
            20                  25

<210> SEQ ID NO 33
<211> LENGTH: 409
<212> TYPE: PRT
<213> ORGANISM: Artificial Sequence
<220> FEATURE:
<223> OTHER INFORMATION: synthetic

<400> SEQUENCE: 33

Met Lys Lys Thr Ala Ile Ala Ile Ala Val Ala Leu Ala Gly Phe Ala
1               5                   10                  15

Thr Val Ala Gln Ala Lys Ile Glu Glu Gly Lys Leu Val Ile Trp Ile
            20                  25                  30

Asn Gly Asp Lys Gly Tyr Asn Gly Leu Ala Glu Val Gly Lys Lys Phe
        35                  40                  45

Glu Lys Asp Thr Gly Ile Lys Val Thr Val Glu His Pro Asp Lys Leu
    50                  55                  60

Glu Glu Lys Phe Pro Gln Val Ala Ala Thr Gly Asp Gly Pro Asp Ile
65                  70                  75                  80

Ile Phe Trp Ala His Asp Arg Phe Gly Gly Tyr Ala Gln Ser Gly Leu
                85                  90                  95

Leu Ala Glu Ile Thr Pro Asp Lys Ala Phe Gln Asp Lys Leu Tyr Pro
            100                 105                 110

Phe Thr Trp Asp Ala Val Arg Tyr Asn Gly Lys Leu Ile Ala Tyr Pro
        115                 120                 125

Ile Ala Val Glu Ala Leu Ser Leu Ile Tyr Asn Lys Asp Leu Leu Pro
    130                 135                 140
```

Asn Pro Pro Lys Thr Trp Glu Glu Ile Pro Ala Leu Asp Lys Glu Leu
145                 150                 155                 160

Lys Ala Lys Gly Lys Ser Ala Leu Met Phe Asn Leu Gln Glu Pro Tyr
            165                 170                 175

Phe Thr Trp Pro Leu Ile Ala Ala Asp Gly Gly Tyr Ala Phe Lys Tyr
            180                 185                 190

Glu Asn Gly Lys Tyr Asp Ile Lys Asp Val Gly Val Asp Asn Ala Gly
            195                 200                 205

Ala Lys Ala Gly Leu Thr Phe Leu Val Asp Leu Ile Lys Asn Lys His
        210                 215                 220

Met Asn Ala Asp Thr Asp Tyr Ser Ile Ala Glu Ala Ala Phe Asn Lys
225                 230                 235                 240

Gly Glu Thr Ala Met Thr Ile Asn Gly Pro Trp Ala Trp Ser Asn Ile
                245                 250                 255

Asp Thr Ser Lys Val Asn Tyr Gly Val Thr Val Leu Pro Thr Phe Lys
                260                 265                 270

Gly Gln Pro Ser Lys Pro Phe Val Gly Val Leu Ser Ala Gly Ile Asn
            275                 280                 285

Ala Ala Ser Pro Asn Lys Glu Leu Ala Lys Glu Phe Leu Glu Asn Tyr
        290                 295                 300

Leu Leu Thr Asp Glu Gly Leu Glu Ala Val Asn Lys Asp Lys Pro Leu
305                 310                 315                 320

Gly Ala Val Ala Leu Lys Ser Tyr Glu Glu Leu Ala Lys Asp Pro
                325                 330                 335

Arg Ile Ala Ala Thr Met Glu Asn Ala Gln Lys Gly Glu Ile Met Pro
                340                 345                 350

Asn Ile Pro Gln Met Ser Ala Phe Trp Tyr Ala Val Arg Thr Ala Val
            355                 360                 365

Ile Asn Ala Ala Ser Gly Arg Gln Thr Val Asp Glu Ala Leu Lys Asp
        370                 375                 380

Ala Gln Thr Ala His Ile Val Met Val Asp Ala Tyr Lys Pro Thr Lys
385                 390                 395                 400

Gly Ala Pro His His His His His His
                405

<210> SEQ ID NO 34
<211> LENGTH: 289
<212> TYPE: PRT
<213> ORGANISM: Artificial Sequence
<220> FEATURE:
<223> OTHER INFORMATION: synthetic

<400> SEQUENCE: 34

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly Ser Phe
            20                  25                  30

Ser Met Ser Trp Val Arg Gln Ala Pro Gly Gly Leu Glu Trp Val
        35                  40                  45

Ala Gly Leu Ser Ala Arg Ser Ser Leu Thr His Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

```
Ala Arg Arg Ser Tyr Asp Ser Ser Gly Tyr Trp Gly His Phe Tyr Ser
            100                 105                 110

Tyr Met Asp Val Trp Gly Gln Gly Thr Leu Val Thr Val Ser Ser Gly
        115                 120                 125

Gly Gly Gly Ser Gly Gly Gly Ser Gly Gly Gly Ser Gln Ser
    130                 135                 140

Val Leu Thr Gln Pro Ser Ser Val Ser Ala Ala Pro Gly Gln Lys Val
145                 150                 155                 160

Thr Ile Ser Cys Ser Gly Ser Thr Ser Asn Ile Gly Asn Asn Tyr Val
                165                 170                 175

Ser Trp Tyr Gln Gln His Pro Gly Lys Ala Pro Lys Leu Met Ile Tyr
            180                 185                 190

Asp Val Ser Lys Arg Pro Ser Gly Val Pro Asp Arg Phe Ser Gly Ser
        195                 200                 205

Lys Ser Gly Asn Ser Ala Ser Leu Asp Ile Ser Gly Leu Gln Ser Glu
    210                 215                 220

Asp Glu Ala Asp Tyr Tyr Cys Ala Ala Trp Asp Ser Leu Ser Glu
225                 230                 235                 240

Phe Leu Phe Gly Thr Gly Thr Lys Leu Thr Val Leu Gly Gln Glu Phe
                245                 250                 255

Asp Tyr Lys Asp Asp Asp Lys Gly Gly Ser Ala His Ile Val Met
            260                 265                 270

Val Asp Ala Tyr Lys Pro Thr Lys Gly Ala Pro His His His His
        275                 280                 285

His

<210> SEQ ID NO 35
<211> LENGTH: 270
<212> TYPE: PRT
<213> ORGANISM: Artificial Sequence
<220> FEATURE:
<223> OTHER INFORMATION: synthetic

<400> SEQUENCE: 35

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Gly Ser Phe
            20                  25                  30

Ser Met Ser Trp Val Arg Gln Ala Pro Gly Gly Leu Glu Trp Val
        35                  40                  45

Ala Gly Leu Ser Ala Arg Ser Ser Leu Thr His Tyr Ala Asp Ser Val
50                  55                  60

Lys Gly Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Ala Arg Arg Ser Tyr Asp Ser Ser Gly Tyr Trp Gly His Phe Tyr Ser
            100                 105                 110

Tyr Met Asp Val Trp Gly Gln Gly Thr Leu Val Thr Val Ser Ser Gly
        115                 120                 125

Gly Gly Gly Ser Gly Gly Gly Ser Gly Gly Gly Ser Gln Ser
    130                 135                 140

Val Leu Thr Gln Pro Ser Ser Val Ser Ala Ala Pro Gly Gln Lys Val
145                 150                 155                 160
```

```
Thr Ile Ser Cys Ser Gly Ser Thr Ser Asn Ile Gly Asn Asn Tyr Val
                165                 170                 175

Ser Trp Tyr Gln Gln His Pro Gly Lys Ala Pro Lys Leu Met Ile Tyr
                180                 185                 190

Asp Val Ser Lys Arg Pro Ser Gly Val Pro Asp Arg Phe Ser Gly Ser
            195                 200                 205

Lys Ser Gly Asn Ser Ala Ser Leu Asp Ile Ser Gly Leu Gln Ser Glu
        210                 215                 220

Asp Glu Ala Asp Tyr Tyr Cys Ala Ala Trp Asp Asp Ser Leu Ser Glu
225                 230                 235                 240

Phe Leu Phe Gly Thr Gly Thr Lys Ala His Ile Val Met Val Asp Ala
                245                 250                 255

Tyr Lys Pro Thr Lys Gly Ala Pro His His His His His His
                260                 265                 270

<210> SEQ ID NO 36
<211> LENGTH: 16
<212> TYPE: PRT
<213> ORGANISM: Artificial Sequence
<220> FEATURE:
<223> OTHER INFORMATION: synthetic

<400> SEQUENCE: 36

Arg Gly Val Pro His Ile Val Met Val Asp Ala Tyr Lys Arg Tyr Lys
1                   5                   10                  15
```